US012765800B2

(12) United States Patent
Tsouluhas

(10) Patent No.: US 12,765,800 B2
(45) Date of Patent: Oct. 20, 2026

(54) SYSTEM AND METHOD FOR MEASURING INSPIRATORY/EXPIRATORY AIR FLOW

(71) Applicant: CDM Montreal, Montreal (CA)

(72) Inventor: Anna Tsouluhas, Mount-Royal (CA)

(73) Assignee: CDM MONTREAL, Montreal (CA)

( * ) Notice: Subject to any disclaimer, the term of this patent is extended or adjusted under 35 U.S.C. 154(b) by 893 days.

(21) Appl. No.: 17/584,719

(22) Filed: Jan. 26, 2022

(65) Prior Publication Data

US 2022/0233094 A1 Jul. 28, 2022

Related U.S. Application Data

(63) Continuation of application No. PCT/CA2022/050102, filed on Jan. 26, 2022.

(Continued)

(51) Int. Cl.
*A61B 5/087* (2006.01)
*A61B 5/00* (2006.01)

(Continued)

(52) U.S. Cl.
CPC ............ *A61B 5/087* (2013.01); *A61B 5/0022* (2013.01); *A61B 5/0803* (2013.01); *A61B 5/097* (2013.01); *A61B 5/7435* (2013.01); *A61B 7/003* (2013.01)

(58) Field of Classification Search
CPC ..... A61B 5/087; A61B 5/0022; A61B 5/0803; A61B 5/097; A61B 5/7435; A61B 7/003;

(Continued)

(56) References Cited

U.S. PATENT DOCUMENTS 10,272,215 B2 4/2019 Adams et al.
2007/0276278 A1* 11/2007 Coyle .................... A61B 5/369 600/301

(Continued)

FOREIGN PATENT DOCUMENTS

WO WO-2015052519 A1 * 4/2015 .......... A61M 15/008

OTHER PUBLICATIONS

International Search Report and Written Opinion of PCT/CA2022/050102, May 3, 2022, 10 pages.

(Continued)

*Primary Examiner* — Devin B Henson
*Assistant Examiner* — Kavya Shobana Balaji
(74) *Attorney, Agent, or Firm* — Merchant & Gould P.C.

(57) ABSTRACT

A method and a system for measuring inspiratory/expiratory air flow rate from inhalation/expiration near a microphone of an electronic device by a user. An inhaler is selected by the user among a plurality of possible inhalers, and the user is prompted to perform an inhalation/expiration close to a microphone of the computing device. Sound is measured during inhalation/expiration and sound data derived therefrom. There is determined the inspiratory/expiratory air flow rate by comparing the collected sound data with a flow rate data set used by the industrially calibrated device and stored in an inhaler-appropriate flow-rate database. The system determines whether the selected inhaler is one of the appropriate inhalers for the inspiratory/expiratory flow measured by comparing the determined inspiratory/expiratory air flow rate with a range of inspiratory/expiratory air flow rates corresponding to the selected inhaler.

19 Claims, 18 Drawing Sheets

Related U.S. Application Data

(60) Provisional application No. 63/141,759, filed on Jan. 26, 2021.

(51) Int. Cl.

*A61B 5/08* (2006.01)
*A61B 5/097* (2006.01)
*A61B 7/00* (2006.01)

(58) Field of Classification Search

CPC .... A61B 2560/0228; A61B 2562/0204; A61B 5/6898; A61B 5/4842; A61B 5/7246; A61B 5/7275; A61B 5/486; A61B 5/7475; A61B 5/091; A61B 2505/09; A61B 2560/0242; A61B 2560/0475; A61B 5/085; A61B 5/48; A61B 5/4833; A61B 5/4839; A61B 5/7203; A61B 5/742; A61B 7/04; A61B 2562/0219; A61B 2576/00; A61B 5/0077; A61B 5/0816; A61B 5/082; A61B 5/0823; A61B 5/1123; A61B 5/1128; A61B 5/7425; G16H 10/00

See application file for complete search history.

(56) References Cited

U.S. PATENT DOCUMENTS

| | | | | |
|---|---|---|---|---|
| 2010/0324417 | A1 | 12/2010 | McNair | |
| 2015/0283337 | A1* | 10/2015 | Adams | A63B 21/0088 128/203.15 |
| 2016/0007913 | A1* | 1/2016 | Darket | A61B 5/7246 600/538 |
| 2017/0100550 | A1* | 4/2017 | Van De Laar | A61B 5/087 |
| 2017/0296094 | A1* | 10/2017 | Fonzi, III | A61B 5/0002 |
| 2018/0008192 | A1 | 1/2018 | Matthewson | |
| 2018/0064402 | A1* | 3/2018 | Leydon | A61M 15/0021 |
| 2018/0092595 | A1* | 4/2018 | Chen | A61B 5/1123 |
| 2019/0192046 | A1* | 6/2019 | Ljungberg | G16H 20/10 |
| 2021/0393892 | A1* | 12/2021 | Zur | A61M 15/008 |
| 2022/0031973 | A1* | 2/2022 | Matthewson | A61M 15/00 |

OTHER PUBLICATIONS

Supplementary European Search Report from European Patent Office dated Nov. 15, 2024, for European Application No. EP 22744959.

* cited by examiner

SYSTEM AND METHOD FOR MEASURING INSPIRATORY/EXPIRATORY AIR FLOW

RELATED APPLICATION

The present application claims priority to or benefit of U.S. provisional patent application No. 63/141,759, filed Jan. 26, 2021, which is incorporated herein by reference in its entirety.

TECHNICAL FIELD

The subject matter disclosed generally relates to measurement devices for inspiratory/expiratory flow measurement. More specifically, it relates to a method for measuring an inspiratory/expiratory flow using a microphone of a computing device.

BACKGROUND

Presently, on the market, there is a device called the In-Check DIAL™, which is a hand-held low-range inspiratory flow measurement device with a dial top used to accurately simulate the resistance of inhaler devices. In previous years, prior to the COVID-19 pandemic, physicians would be given the In-Check DIAL™ device for a period of time, to be used with users, to help them understand the difference in inspiratory effort required to properly inhale their medications using a given type of inhaler.

Choosing a type of inhaler based on Peak Inspiratory Flow Rate (PIFR) is important to ensure users receive the adequate dose of their medication.

The purpose of the In-Check DIAL™ is primarily to provide physicians and their users with a measurement tool to help them understand the inspiratory flow required by users to properly use different devices such as, for example, different inhalers which can be of different types. Knowing the required (or desired) inspiratory flow allows the physicians to recommend the appropriate device (inhaler type, and specific inhaler within the type) for different users, based on their ability to inhale. At the same time, using the In-Check DIAL™ may provide the user with an experience of different devices including, but not limited to, dry power inhaler (DPI), soft mist inhaler (SMI), and pressurized metered-dose inhalers (pMDI) to empower the user to be involved in an informed decision about device choice.

In light of the current situation with the COVID-19 pandemic, physicians are unable to use a single In-Check DIAL™ device with multiple users.

SUMMARY

According to an aspect of the disclosure, there is provided a method for measuring an inspiratory air flow rate from an inhalation to a microphone of an electronic device by a user, the electronic device having a display and an input device, the method executable by a processor, the method comprising:

obtaining a selected inhaler as selected by the user among a plurality thereof, and prompting the user to perform an inhalation in close proximity to a microphone of the computing device during a measurement period of time;

measuring a sound signal during the inhalation by the microphone and generating a sound data based on the sound signal during the inhalation performed during the measurement period of time;

based on the sound data, determining, by the processor, an inspiratory air flow rate by comparing the collected sound data with a flow rate data set used by the industrially calibrated device and stored in an inhaler-appropriate flow-rate database;

determining, by the processor, if the inspiratory air flow rate is within a predetermined range for the selected inhaler;

determining whether the selected inhaler is one of the appropriate inhalers for the inspiratory flow measured by comparing the determined inspiratory air flow rate with a range of inspiratory air flow rate corresponding to the selected inhaler; and based on determining that the selected inhaler is one of the appropriate inhalers, generating and displaying a conclusion message on the display of the computing device.

According to another aspect of the disclosure, there is provided a method for measuring an expiratory air flow rate from an exhalation to a microphone of an electronic device by a user, the electronic device having a display and an input device, the method executable by a processor, the method comprising: obtaining a selected inhaler as selected by the user among a plurality thereof, and prompting the user to perform an exhalation in close proximity to a microphone of the computing device during a measurement period of time; measuring a sound signal during the exhalation by the microphone and generating a sound data based on the sound signal during the exhalation performed during the measurement period of time; based on the sound data, determining, by the processor, an expiratory air flow rate by comparing the collected sound data with a flow rate data set used by the industrially calibrated device and stored in an inhaler-appropriate flow-rate database; determining, by the processor, if the expiratory air flow rate is within a predetermined range for the selected inhaler; determining whether the selected inhaler is one of the appropriate inhalers for the expiratory flow measured by comparing the determined expiratory air flow rate with a range of expiratory air flow rate corresponding to the selected inhaler; and based on determining that the selected inhaler is one of the appropriate inhalers, generating and displaying a conclusion message on the display of the computing device.

According to another aspect of the disclosure, there is provided a method for measuring an inspiratory/expiratory air flow rate from an inhalation/exhalation to a microphone of an electronic device by a user, the electronic device having a display and an input device, the method executable by a processor, the method comprising: obtaining a selected inhaler as selected by the user among a plurality thereof, and prompting the user to perform an inhalation/exhalation in close proximity to a microphone of the computing device during a measurement period of time; measuring a sound signal during the inhalation/exhalation by the microphone and generating a sound data based on the sound signal during the inhalation/exhalation performed during the measurement period of time; based on the sound data, determining, by the processor, an inspiratory/expiratory air flow rate by comparing the collected sound data with a flow rate data set used by the industrially calibrated device and stored in an inhaler-appropriate flow-rate database; determining, by the processor, if the inspiratory/expiratory air flow rate is within a predetermined range for the selected inhaler; determining whether the selected inhaler is one of the appropriate inhalers for the inspiratory/expiratory flow measured by comparing the determined inspiratory/expiratory air flow rate with a range of inspiratory/expiratory air flow rate corresponding to the selected inhaler; and based on determining that the selected inhaler is one of the appropriate inhalers, generating and displaying a conclusion message on the display of the computing device.

According to an embodiment, generating the sound data based on the sound signal comprises attenuating the sound signal based on the microphone sensitivity determined for the selected inhaler.

According to an embodiment, the microphone sensitivity is determined by retrieving, from a microphone sensitivity database, a value of the microphone sensitivity associated with the inhaler identifier associated with the selected inhaler.

According to an embodiment, the microphone sensitivity database is located locally on the electronic device.

According to an embodiment, the microphone sensitivity database is located remotely on the remote server.

According to an embodiment, there is further provided the step of adjusting the microphone sensitivity prior to measuring the sound data.

According to an embodiment, generating and displaying the conclusion message on the display of the computing device comprises: in response to determining that the selected type of the inhaler is one of the appropriate types of the inhaler, generating and displaying a message on the display of the computing device that the selected type of the inhaler is one of the appropriate types of the inhaler.

According to an embodiment, the conclusion message is generated based on determining whether an inhaler identifier associated with the selected inhaler is within the range of inspiratory flow corresponding to the selected inhaler.

According to an embodiment, the range of inspiratory flow corresponding to the selected inhaler is stored in a remote database located on the remote server.

According to an embodiment, the selected inhaler comprises other inhalers being of the same type of the inhalers.

According to an embodiment, the processor is the processor of the electronic device.

According to an embodiment, obtaining the selected inhaler comprises prompting the user to select, using the input device, an inhaler among inhalers rendered on the display to indicate the selected inhaler.

According to another aspect of the disclosure, there is provided a system for measuring an air flow rate from an inhalation, the system comprising: a display and an input device, a microphone sensitivity database comprising a plurality of pairs of microphone sensitivity values and inhaler identifiers; an inhaler-appropriate flow-rate database comprising predetermined ranges for inhalers and inhaler identifiers; and a microphone configured to measure a sound signal during the inhalation, a local processor coupled to a remote processor, both configured to:

receive a selection of an inhaler among inhalers rendered on the display to indicate a selected inhaler, and prompt the user to perform an inhalation in close proximity to a microphone of the computing device during a measurement period of time;

generate, by the local processor, a sound data based on the sound signal during the inhalation performed during the measurement period of time;

based on the sound data, determine an inspiratory air flow rate by comparing the sound data with a flow rate data set used by the industrially calibrated device and stored in the calibration database;

determine whether the inspiratory flow rate is within a predetermined range for the selected inhaler;

determine whether the selected inhaler is one of the appropriate inhalers for the inspiratory flow measured by comparing the inspiratory flow with a range of inspiratory flow corresponding to the selected inhaler; and based on determining that the selected inhaler is one of the appropriate inhalers, generate a conclusion message on the display of the computing device.

According to an aspect of the disclosure, there is provided a system for measuring an air flow rate from an exhalation, the system comprising: a display and an input device, a microphone sensitivity database comprising a plurality of pairs of microphone sensitivity values and inhaler identifiers; an inhaler-appropriate flow-rate database comprising predetermined ranges for inhalers and inhaler identifiers; and a microphone configured to measure a sound signal during the exhalation, a local processor coupled to a remote processor, both configured to: receiving a selection of an inhaler among inhalers rendered on the display to indicate a selected inhaler, and prompt the user to perform an exhalation in close proximity to a microphone of the computing device during a measurement period of time; generate, by the local processor, a sound data based on the sound signal during the exhalation performed during the measurement period of time; based on the sound data, determine an expiratory air flow rate by comparing the sound data with a flow rate data set used by the industrially calibrated device and stored in the calibration database; determine whether the expiratory flow rate is within a predetermined range for the selected inhaler; determine whether the selected inhaler is one of the appropriate inhalers for the expiratory flow measured by comparing the expiratory flow with a range of expiratory flow corresponding to the selected inhaler; and based on determining that the selected inhaler is one of the appropriate inhalers, generate a conclusion message on the display of the computing device.

According to an aspect of the disclosure, there is provided a system for measuring an air flow rate from an inhalation/exhalation, the system comprising: a display and an input device, a microphone sensitivity database comprising a plurality of pairs of microphone sensitivity values and inhaler identifiers; an inhaler-appropriate flow-rate database comprising predetermined ranges for inhalers and inhaler identifiers; and a microphone configured to measure a sound signal during the inhalation/exhalation, a local processor coupled to a remote processor, both configured to: receiving a selection of an inhaler among inhalers rendered on the display to indicate a selected inhaler, and prompt the user to perform an inhalation/exhalation in close proximity to a microphone of the computing device during a measurement period of time; generate, by the local processor, a sound data based on the sound signal during the inhalation/exhalation performed during the measurement period of time; based on the sound data, determine an inspiratory/expiratory air flow rate by comparing the sound data with a flow rate data set used by the industrially calibrated device and stored in the calibration database; determine whether the inspiratory/expiratory flow rate is within a predetermined range for the selected inhaler; determine whether the selected inhaler is one of the appropriate inhalers for the inspiratory flow measured by comparing the inspiratory/expiratory flow with a range of inspiratory/expiratory flow corresponding to the selected inhaler; and based on determining that the selected inhaler is one of the appropriate inhalers, generate a conclusion message on the display of the computing device.

According to an embodiment, the sound data being generated comprises the sound signal attenuated based on the microphone sensitivity determined for the selected inhaler.

According to an embodiment, the microphone sensitivity is determined by retrieving, from a microphone sensitivity database, a value of the microphone sensitivity associated with the inhaler identifier associated with the selected inhaler.

According to an embodiment, the microphone sensitivity database is located locally on the electronic device.

According to an embodiment, the microphone sensitivity database is located remotely on the remote server.

According to an embodiment, the microphone sensitivity is adjusted prior to measuring the sound data.

According to an embodiment, the conclusion message is generated based on determining whether an inhaler identifier associated with the selected inhaler is within the range of inspiratory/expiratory flow corresponding to the selected inhaler.

According to an embodiment, the processor is the processor of the electronic device.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
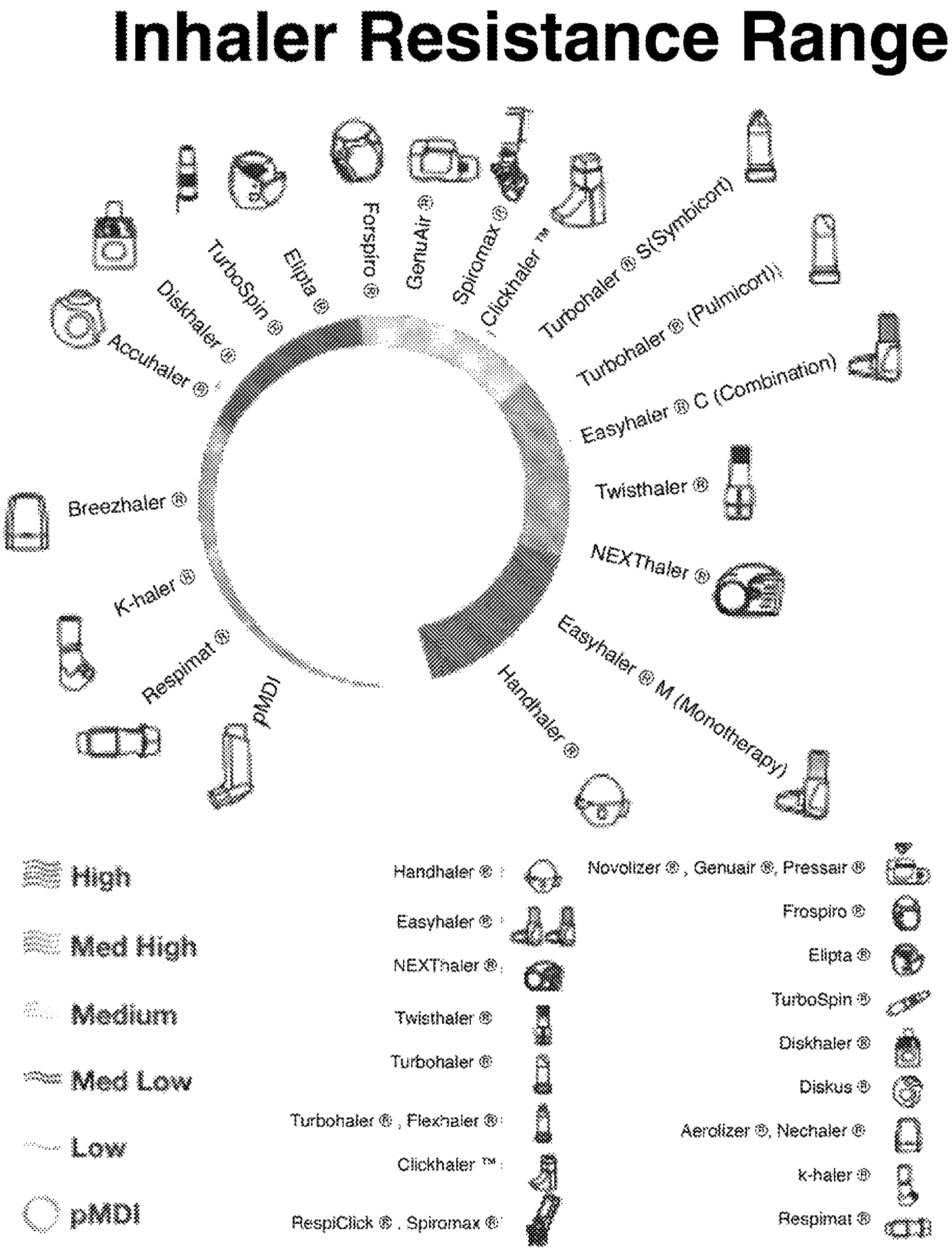
FIG. 1 is a diagram illustrating the required inspiratory flow rate for using different specific inhalers or types of inhalers, according to the state of the art.

The In-Check DIAL™ device demonstrates that not all inhalers are the same. Some inhalers require significantly higher inspiratory effort to adequately inhale the medication. This is shown in FIG. 1, which provides a diagram illustrating the required inspiratory flow rate for using different specific inhalers or types of inhalers, according to the state of the art. As can be seen, the required inspiratory flow rate is the lowest for pMDI in FIG. 1 and the highest for the Handihaler™.

Many users do not use their inhalers correctly, failing to inhale at the correct flow rate, thus requiring an assessment of their flow rate using the industrially-calibrated flow measurement device such as the In-Check DIAL™ device to make this assessment. The user's inhaleability may be evaluated with such the industrially-calibrated flow measurement device to ensure the user's ability or capability of inhaling at a proper rate to meet the medication administration requirements of an inhaling device.

Figure 2:
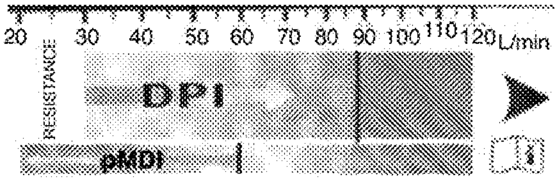
FIG. 2 is a diagram illustrating the ideal inspiratory flow rate ranges for using different types of inhalers (dry powder inhaler, DPI, or pressurized metered-dose inhaler, pMDI), according to the state of the art.

FIG. 2 provides a diagram illustrating the ideal inspiratory flow rate ranges for using different types of inhalers (dry powder inhaler, DPI, or pressurized metered-dose inhaler, pMDI), according to the state of the art.

In light of the current situation with the COVID-19 pandemic, physicians are unable to use a single In-Check DIAL™ device with multiple users, or simply unable to see their users and use the In-Check DIAL™ device.

There is therefore a difficulty of being able to measure the suitability of the maximum inhalation flow rate capability of an individual in comparison with the inhalation device used or considered for use by that individual in the absence of an appropriate measurement apparatus, either because of the remoteness of the individual or because of hygienic reasons in view of which the measurement apparatus is not reused.

The technology as described herein uses an existing device to determine an appropriate inhaler. In particular, the technology as described herein uses user's own computing device (also referred to herein as "electronic device"), which the user already owns, and which is primarily not dedicated to flow measurements. In particular, without the microphone and the instructions of the computing device is not capable to determine an air flow rate; however, such a computing device comprises a microphone for measuring a sound signal.

The system and the method as described herein help to assess the inspiratory effort of the user, thereby providing physicians and their users with an individualized measurement tool to evaluate inspiratory effort and to help select inhaler devices for, for example, a chronic obstructive pulmonary disease (COPD). The system and the method as described herein uses the existing microphone technology inside or coupled to the electronic devices (such as, for example, mobile phones) to assess airflow. The person's inhalation effort is then validated against the data set used by the commercially available In-Check DIAL™.

The system as described herein allows users to measure their ability to inhale in a context where mechanically-operated flow-measurement devices such as In-Check DIAL™ are not available. Using the system as described herein and with TM the method being executed, the health-care professionals may show users the importance of inhaling correctly and make data-based recommendations. With the application installed and executed by the computing device 1010, the system 1000 simulates the resistance characteristics of the specific inhaler of a user and measures the peak inspiratory flow rate. By correlating microphone sensitivity to inhaler resistance, the system and the method as described herein permits to measure inspiratory flow rate relative to inhaler resistance and to assess whether the user has or is capable of an adequate inhalation effort for the COPD inhalers. The system and the method as described herein permits to convert a user's computer device into a flow-measurement device that may be used by the user instead of using the mechanically-operated flow-measurement devices such as In-Check DIAL™.

Although the description provided herein mostly refers to measurement of the sound during the user's inhalation (input, in other word an "inflow", of the air to the user's mouth), the same technology is applicable to the exhalation performed by the user, the sound of which is measured, in accordance with at least one embodiment of the present disclosure. Therefore, the steps of the method as described herein are also applicable to the measurement of the sound produced by the user's exhalation (output, in other word "outflow", of the air from the user's mouth). In such embodiments, the microphone receives an exhaling sound (instead of the inhaling sound 1050 illustrated in FIG. 6).

According to at least one embodiment, the system as described herein is also configured to measure the airflow rate (also referred to herein as an "expiratory air flow rate") from the exhalation. In such embodiments, the sound data is compared to the data available and stored in the databases described herein for the industrially calibrated device. For the measurements of the expiratory air flow rate related to the exhalation, the industrially calibrated device may be, for example, a whistle. For such industrially calibrated devices, the expiratory air flow is assessed based on whether the exhale of the user permits to hit a pre-determined level specified for the industrially calibrated device (for example, the whistle). In at least one embodiment of the present technology, the expiratory air flow rate may be determined by comparing the collected sound data with a flow rate data set (related to the exhalation) and used by the industrially calibrated device. Such a flow rate data set (related to the exhalation) may be stored in the inhaler-appropriate flow-rate database described herein (for example, in addition to the data related to the measurement of the flow rate data set related to the inhalation). The flow rate data set related to the exhalation may be compared to a range of the expiratory air flow rate corresponding to the selected inhaler in a similar manner as described below for the range of inspiratory air flow rate.

In at least one embodiment, the sound data may comprise at least one of the sound of inhalation and the sound of exhalation.

Figure 10:
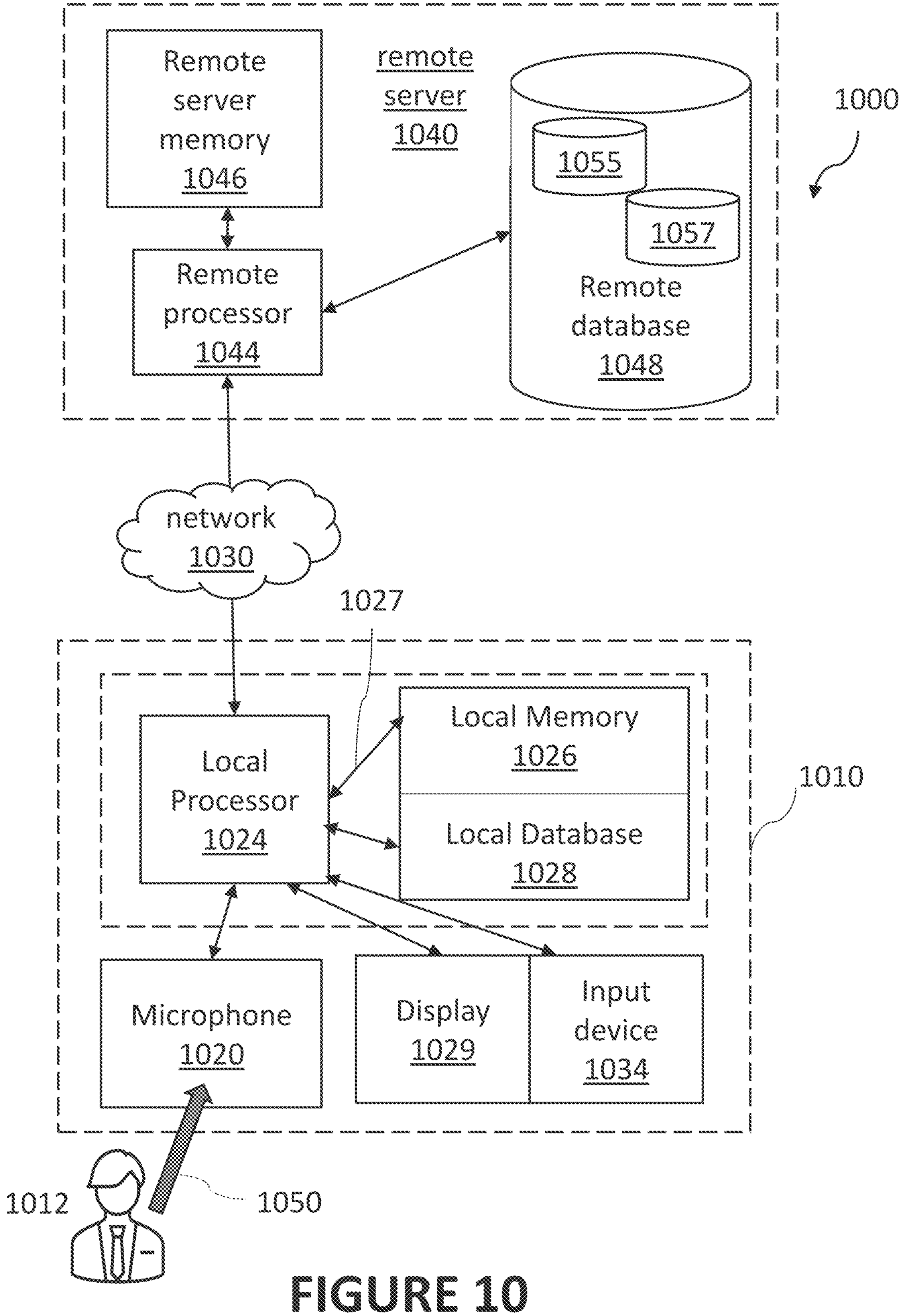
FIG. 10 illustrates a system for measuring an airflow, in accordance with at least one embodiment of the present disclosure.

FIG. 10 illustrates a system 1000 for measuring an airflow, in accordance with at least one embodiment of the present disclosure. The electronic device 1010 is associated with a user 1012. The electronic device 1010 may be, for example and without limitation, a smartphone or the like. For example, the electronic device 1010 may be a tablet computer, smartwatch, smart glasses, wearable device with microphone, laptop computer, tabletop computer with microphone, etc. In all cases, the electronic device 1010 is not dedicated to measuring air flow rates from a person's inhalation/exhalation, i.e., the method is implemented on an electronic device 1010 not specifically designed to be used for this purpose.

The electronic device 1010 comprises a microphone 1020. The microphone 1020 is configured to receive user's sound signal of inhalation/exhalation. In other words, the microphone 1020 is configured to receive and register (measure) an acoustic wave emitted by the user 1012 when the user 1012 inhales. For example, the microphone 1020 may be a built-in microphone, as there is one in a phone or a tablet. In some embodiments, the microphone 1020 may have a body that is separate from the electronic device 1010.

The system and the method as described herein are not limited to using electronic devices 1010 having built-in microphones. Other embodiments are also contemplated and equally possible where the electronic device 1010 (smartphone or otherwise) can receive sound data from an external microphone such as microphone 1020 associated with a headset (wired or wireless) or a standalone microphone. This embodiment is particularly useful with desktop computers having no built-in microphones, or when higher quality microphones are needed/used to capture the sound data, for example, noise-cancelling microphones.

Preferably, the electronic device 1010 is the user's smartphone. In this embodiment, the method as described herein uses the existing, built-in microphone in the smartphone (integrated microphone), or other similar suitable electronic device 1010 having the microphone 1020, to assess or measure air flow rate, especially the peak inspiratory flow rate, as described further below.

The electronic device 1010 also comprises a local processor 1024, an electronic device memory 1026 and a local database 1028. The local processor 1024 may be connected, via a communication network 1030 to a remote server 1040. The remote server 1040 may be implemented as a computer server with a remote processor 1044. The remote server 1040 may be connected to a remote database 1048.

The electronic device 1010 may have various operation systems (OS) and web browsers.

The communication network 1030 may be implemented as, for example, internet, intranet, wide-area communication network, local area communications network, a private communications network and the like, and may be implemented, for example, with wireless and/or wired technology.

The electronic device memory 1026 is configured to store instructions 1027 to be executed by the local processor 1024. The instructions 1027 may be a software application (also referred to herein as an "application") that is executed by the local processor 1024 on the electronic device 1010. The electronic device 1010 may also have speakers that are configured to emit sounds (acoustic waves), for example, with instructions and prompts for the user.

The electronic device 1010 also has a display 1029 that is configured to display various messages when the application is executed by the local processor 1024, in other words, when the computer-executable program instructions are executed by the local processor 1024.

The electronic device 1010 also has an input element. For example, the display 1029 may be a touchscreen that is configured to receive the input from the user 1012 when the user touches the touchscreen at the location of the displayed picture of an inhalator. For example, if the electronic device 1010 is a smartphone, the display 1029 and the input device 1034 may be both implemented as a touchscreen 410.

The electronic device 1010 has an electronic device memory 1026 which may be implemented as a tangible computer-readable storage medium including Read-Only Memory (ROM) and/or Random Access Memory (RAM). The remote server 1040 may also have a remote server memory 1046 which may be implemented as a tangible computer-readable storage medium including Read-Only Memory (ROM) and/or Random Access Memory (RAM).

In at least one embodiment, the application is (in other words, the computer-executable program instructions are) downloaded to and installed in the electronic device memory 1026 of the electronic device 1010. The application is executed by the local processor 1024.

The execution of the application along with the measurement of the inhaling sound by the microphone 1020 provides similar outcome as the use of the In-Check DIAL™ device. The execution of the application along with the measurement of the inhaling sound 1050 helps to provide information on an adequate inspiratory flow rate for the user 1012, and therefore the physicians and the users may make decisions with regards to the inhaler(s) to choose based on the inspiratory effort of the users. Thus, users can receive the adequate doses of medication for different inhalers (for example, DPI, SMI, pMDI).

FIGS. 4-9 illustrate execution of steps of the method as described herein, such as providing instructions to the user and the displaying visual results of conducting the method.

Figure 4:
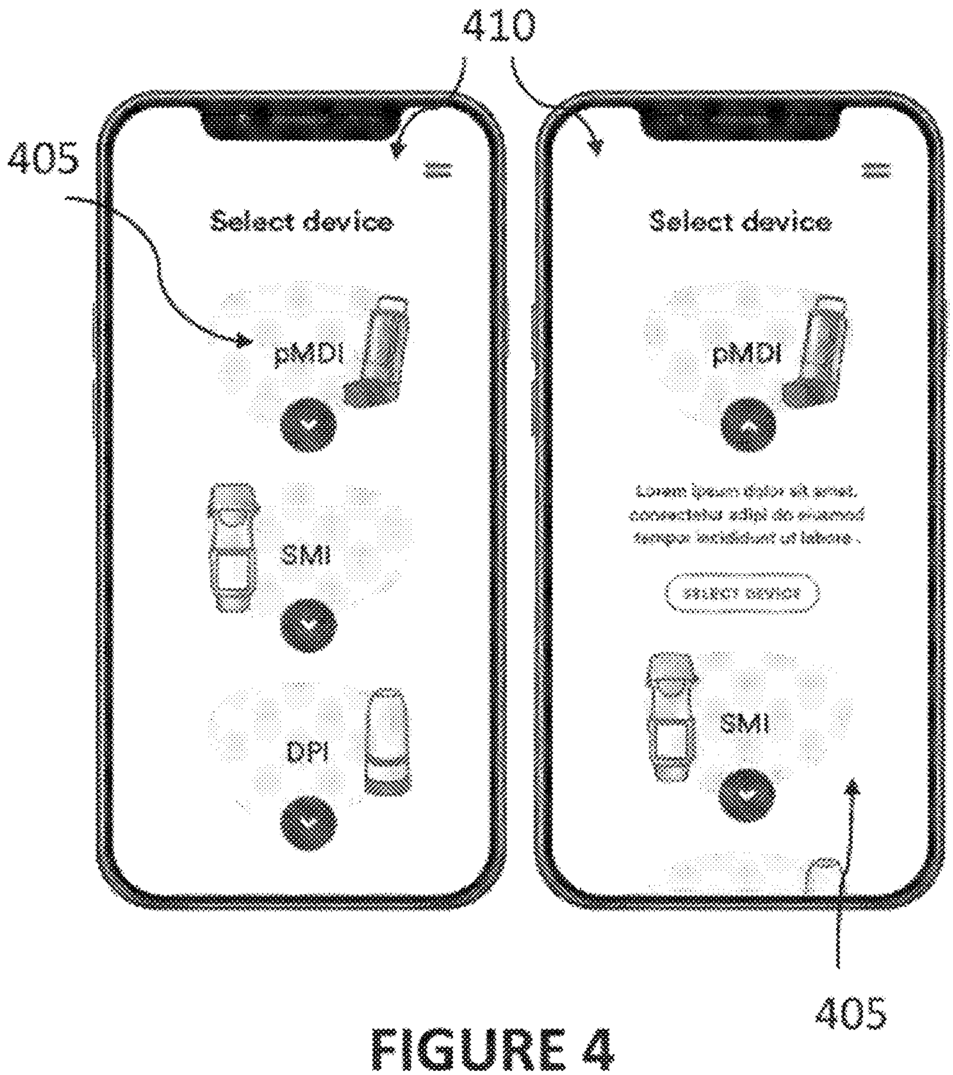
FIG. 4 is a front view illustrating a smartphone with a graphical user interface for making a selection among different types of inhalers, according to an embodiment of the invention.

Referring to FIG. 4, in operation, the local processor 1024 displays on the display 1029 one or more inhaler-selection messages 405. The inhaler-selection message 405 prompts the user to select a type of an inhaler or the inhaler (referred to herein as a "selected inhaler") using the input device of the computing device. The selected inhaler may be a current inhaler that the user is using or an inhaler suggested by the health professional. The selected inhaler corresponds to a selected inhaler identifier that permits to identify the selected inhaler in the databases as described herein.

In FIG. 4, it shown that the user should first select a device on the graphical user interface (such as the touch screen of the smartphone). A selection of types of inhalers or specific inhalers is shown, and the user should look for the appropriate or most familiar device in the categories or examples listed. The categories may include, without limitation, pressurized metered dose inhalers (pMDI), dry powder inhalers (DPI) and soft mist inhalers (SMI).

The user then selects the inhaler by pressing the touchscreen 410.

In response to receiving the user's selection of the inhaler, the local processor 1024 adjusts the microphone sensitivity. Alternatively, the microphone sensitivity may be adjusted right after or simultaneously with prompting the user 1012 to perform an inhalation/exhalation as discussed below.

To measure the user's peak inspiratory flow rate, the application adjusts the microphone sensitivity of the microphone 1020 to match the expected airflow for the selected inhaler type. In other words, based on the selected type of the inhaler, and/or based on the selected inhaler, the local processor 1024 adjusts the microphone sensitivity.

Typically, a microphone sensitivity rating indicates the microphone's output signal strength per unit of sound pressure. The microphone sensitivity may also be expressed as a ratio where 100% microphone sensitivity corresponds to an intrinsic pre-determined microphone sensitivity based on the manufacturer's settings of the microphone. Based on the pre-determined manufacturer's settings of the microphone corresponding to 100% of microphone sensitivity, the microphone sensitivity may be adjusted for various types of inhalers.

Figure 3:
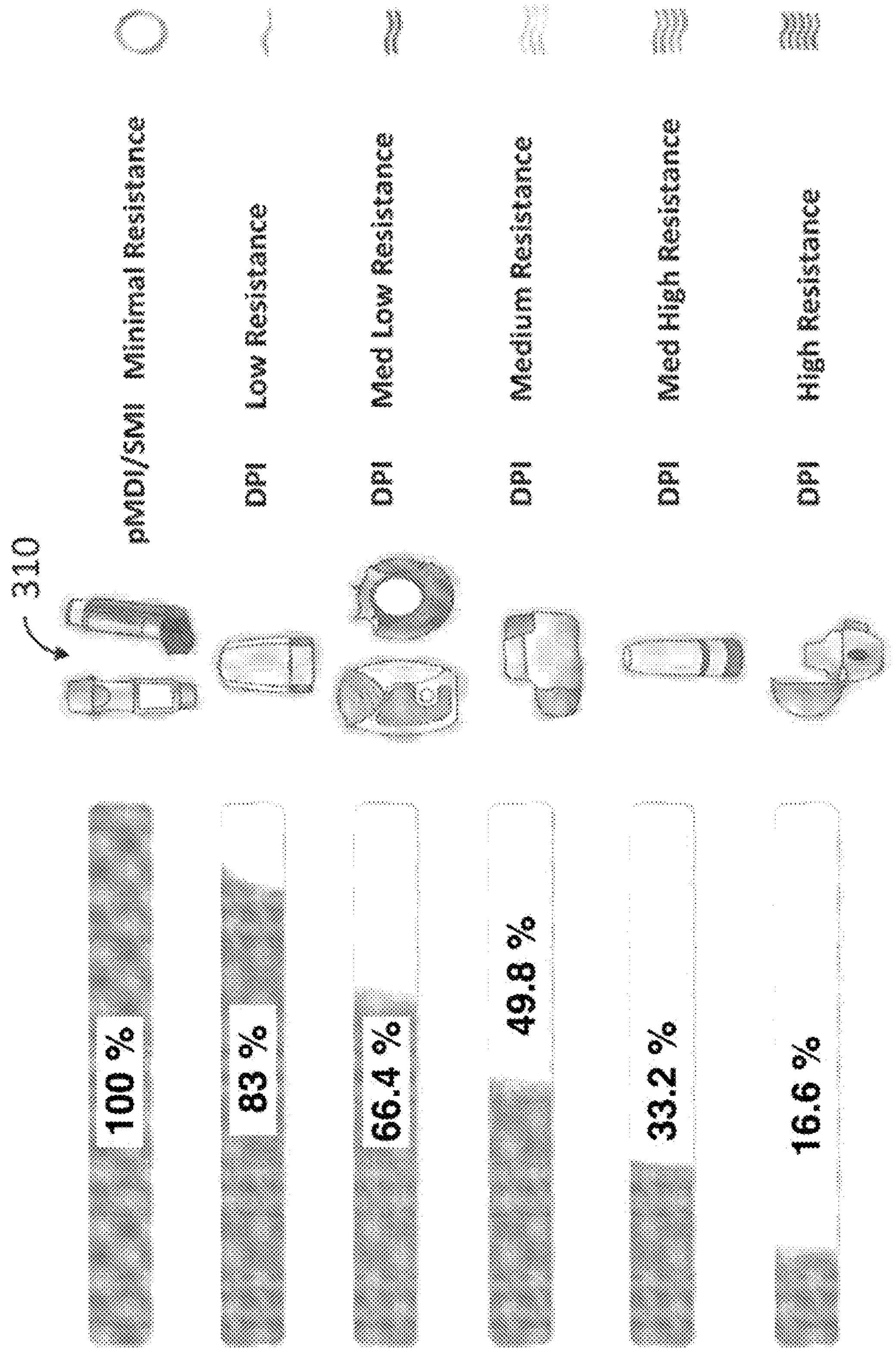
FIG. 3 is a diagram illustrating, from a given peak flow rate measurement, the percentage of the minimum required inspiratory flow rate that was reached for using different types of inhalers, according to an embodiment of the invention.

FIG. 3 illustrates converting the microphone sensitivity of the electronic device 1010 to flow resistance ranges for known types of inhalers 310 based on data for other, already calibrated, industrially-calibrated flow measurement devices (such as the In-Check Dial™).

Referring again to FIG. 3, in at least one embodiment, 100% microphone sensitivity replicates the Minimal Resistance setting on the In-Check Dial™. Such minimal resistance may correspond, for example, to pMDI and SMI inhalers. In other words, to properly measure the air flow, the In-Check Dial™ is set to the minimal resistance. Therefore, to perform measurement of the flow for pMDI and SMI inhalers without the In-Check Dial™, the system 1000 emulates minimal resistance by maintaining 100% of the microphone resistivity.

In at least one embodiment, 83% microphone sensitivity replicates the Low Resistance setting on the In-Check Dial™, which corresponds to DPI inhalers. Still referring to FIG. 3, such minimal resistance may correspond, for example, to DPI inhalers. In other words, to properly measure the air flow, the In-Check Dial™ is set to "low resistance". In at least one embodiment, to perform measurement of the flow for pMDI and SMI inhalers without the In-Check Dial™ the system 1000 emulates low resistance by maintaining 93% of the microphone resistivity.

In at least one embodiment, adjusting the microphone sensitivity to be 66.4% microphone sensitivity and maintaining such a microphone sensitivity by the system 1000 during the execution of the method as described herein replicates the "Med Low Resistance" setting on the In-Check Dial™, which, for example, corresponds to measurement of the flow for Breezhaler™ inhaler. Similarly, 49.8% microphone sensitivity set by the local processor 1024 at the microphone 1020 replicates the "Medium Resistance" setting on the In-Check Dial™; 33.2% microphone sensitivity replicates the Med High Resistance setting on the In-Check Dial™; and 16.6% microphone sensitivity replicates the High Resistance setting on the In-Check Dial™. All examples are given without being strictly limited to such values.

For example, the local database 1028 may store data on the microphone sensitivity for various resistance settings for measuring air flow corresponding to various inhalers based on the industrially calibrated flow-measurement devices (such as, for example, In-Check Dial™).

A microphone sensitivity database 1057 may comprise various values of microphone sensitivity that should be applied to the inhaling sound received and measured by the microphone 1020 and recorded by the local processor 1024 of the electronic device 1010. Such a microphone sensitivity database 1057 may be stored in the local database 1028 or the remote database 1048.

The microphone sensitivity may be adjusted directly on the microphone 1020 if the microphone 1020 is a digital microphone, or may be applied by the local processor 1024 to the raw audio data received from the microphone 1020. The latter may be performed, for example, if the microphone is not a digital microphone and direct adjustment of the microphone sensitivity is not possible.

Figure 5A:
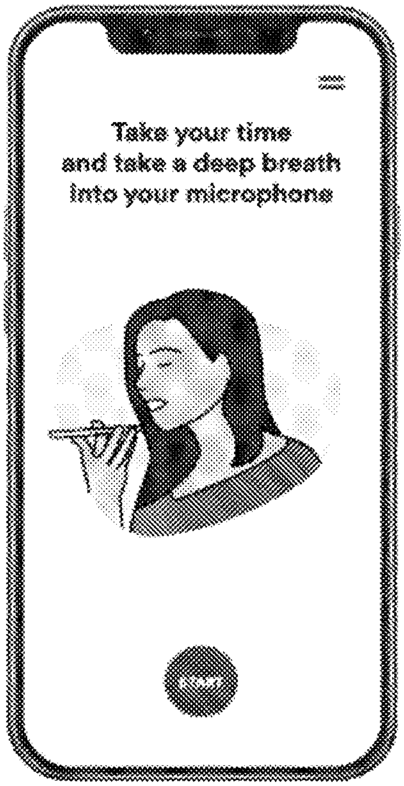
FIG. 5A is a front view illustrating a smartphone with a graphical user interface for instructing a user to inhale properly in close proximity to the smartphone integrated microphone, according to an embodiment of the invention.

The electronic device 1010 is configured to prompt the user 1012, for example, by displaying such a visual prompt or prompting the user with a sound (sound prompt) by the speakers, to perform an inhalation/exhalation by the user. According to an embodiment, and as shown in FIG. 5A, there is shown to the user a visual example of the manner by which inhalation/exhalation should be performed in proximity to the personal computing device's integrated microphone. For example, in FIG. 5A, a short demonstration video and instructions will appear.

Simultaneously with the visual prompt or immediately after such a prompt (visual prompt or sound prompt), the electronic device 1010, and in particular the microphone 1020, measures the sound (acoustic wave) associated to the presumably simultaneous inhalation/exhalation (or, in other words, inspiration/expiration or inflow/outflow of the air to/from the user's mouth).

Referring now to FIG. 5A, after the user 1012 selects the inhaler, the user 1012 is prompted to perform inhalation/exhalation in close proximity to the microphone 1020 of the electronic device 1010. The system 1000, and particular the microphone 1020 with the local processor 1024, then measures the user's inhalation/exhalation effort during a measurement period of time. For example, the measurement period of time may be a pre-determined period of time. Alternatively, the measurement period of time may be determined by the local processor 1024 based on the damped amplitude of the sound signal received and measured by the microphone 1020.

Figure 5B:
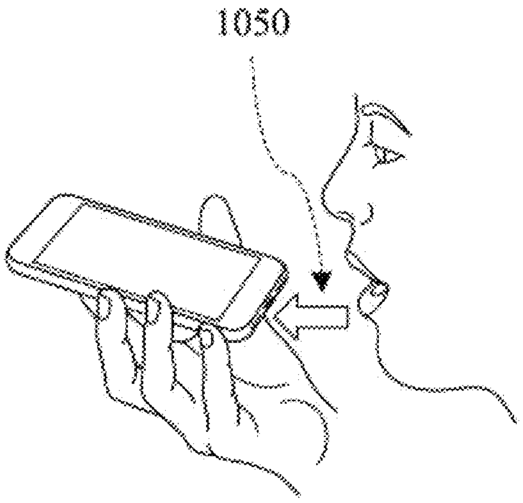
FIG. 5B is a picture illustrating a user inhaling in close proximity to the smartphone integrated microphone, according to an embodiment of the invention.

After careful observation of the prompt with the demonstration, the user then may press START and perform inhalation/exhalation in a similar manner, in close proximity to the personal computing device's integrated microphone, as shown in the photograph of FIG. 5B showing such a real-life operation.

This is the actual step of inhalation/exhalation, from which the sound data is collected for peak inspiratory flow rate assessment for eventual comparison with the flow rate requirements of a given particular inhaler or type of inhaler.

With the microphone sensitivity adjusted, as the user inhales, the microphone 1020 collects sound data when the user inhales as illustrated in FIG. 5B. The sound data is analyzed and reported as a measurement of liter per minute (L/min) based on the sound input to the microphone 1020. The sound data may be stored, for example, locally in the local database 1028. The local processor 1024 processes the collected sound data to assess the respiratory flow of the user 1012. In some embodiments, the sound data may be transmitted to the remote server 1040 for processing by the remote processor.

A peak inspiratory flow rate is then determined. Based on the selected inhaler or selected type of the inhaler, a visual indicator may be displayed on the display 1029 of the electronic device 1010. For example, if the user 1012 has the sufficient peak inspiratory flow rate for the selected inhaler, the visual indicator would land in (would be displayed in) the green zone for that particular inhaler. For example, such visual indicator is displayed on the display 1029 of the electronic device 1010 as a meter of some sort.

Based on a difference in the inspiratory effort required to properly inhale medications, the local processor 1024 then compares the determined respiratory flow of the user 1012 with the required inspiratory effort for the selected inhaler and/or the medication that is used in the selected type of the inhaler. The local processor 1024 then determines an appropriate inhaler and/or appropriate medication for the user based on the determined respiratory flow of the user 1012 and generates and displays a conclusion message with recommendations, in an automated manner.

The scale for correlating the measured sound data with the peak flow rate may be generated by validating the collected sound data with a calibration device similar to or such as, for example, an In-Check DIAL™ device. More specifically, in the application installed on the electronic device 1010, the application is pre-calibrated with help of other already industrially-calibrated flow measurement devices, such as the In-Check DIAL™ device.

To perform a pre-calibration and thus to generate a calibration database 1055, the inhalation/exhalation actions may be performed in a controlled setting with a set of tester users. For example, the calibration database 1055 may be stored in the remote database 1048 and downloaded during the installation of the software application. Alternatively, when executing the instructions, the local processor 1024 may request the remote server 1040 to use the calibration database 1055 located within the remote database 1048 to provide data for the analysis as described here.

During the pre-calibration, for example, the inhalation/exhalation actions are performed both using an electronic device with the microphone similar to the electronic device 1010 (for example, but not limited to a smartphone an integrated microphone) and an industrially calibrated flow measurement device (such as, for example, but not limited to the In-Check DIAL™ device for inhalation, or for example, a whistle for exhalation) together—for the same user and with short difference in time (for example, within the same hour). Thus, each tester uses the industrially calibrated flow measurement device (such as a mechanical measuring device such as the In-Check DIAL™ device) and the electronic device 1010 (which is a non-mechanical measuring device) with calibration instructions installed in the electronic device memory 1026.

To calibrate the application for use on a non-mechanical measuring device, such as electronic device 1010 with the microphone 1020, and therefore to adjust the calibration database 1055, a peak flow rate of that inhalation/exhalation action is determined with the industrially-calibrated flow-measuring devices (such as, for example, the In-Check DIAL™ device), while the sound signal is measured simultaneously by the non-flow measuring device during the calibration to be able to associate a sound intensity to that determined peak flow rate.

Calibration is performed for several inhalation/exhalation actions, preferably by different people (so-called "testers" or "subjects"), thereby associating various sound signal intensity peaks or sound profiles to the peak flow rate determined by industrially calibrated flow-measuring devices (such as, for example, the In-Check DIAL™ device). During the calibration, any measured and recorded sound signal on a smartphone or the like is associated to the peak flow rate, similar to the measurements with the industrially calibrated flow-measuring devices.

Due to such calibration, a user 1012 may later determine an appropriate inhaler when using the electronic device 1010 which is readily available, despite the fact that the electronic device 1010 (for example, smartphone or the like) is by itself unable to measure a flow rate (in other terms, the electronic device 1010 is a non-flow measuring device). Thus, the electronic device 1010 may determine, without having access to the industrially calibrated flow-measuring devices (such as the In-Check DIAL™ device), whether the inhaler and/or the inhaler type of the inhaler used by the user 1012 (or anticipated to be used by the user) is appropriate based on the user's measured inspiratory flow rate.

After the audio data is received from the microphone by the local processor 1024, the processor 1024 analyses (validates) the audio data by comparing the collected audio (sound) data with the flow rate data set used by the industrially calibrated device and stored in the calibration database 1055. For example, the local processor 1024 may compare the highest intensity of the audio data received. In some embodiments, the local processor 1024 may take into account a time-dependent waveform of the received sound data. The system 1000 also takes into account the microphone sensitivity by mapping the microphone sensitivity with the inhaler resistance. The local processor 1024 then generates the value of the inspiratory flow rate based on the audio data.

The system as described herein measures inspiratory flow rate relative to the inhaler resistance to assess whether the user has adequate inhalation/exhalation effort for the chronic obstructive pulmonary disease (COPD) inhalers available on the market.

The flow resistance to overcome with the user's peak respiratory flow (being measured) is dependent on the type of inhaler, as shown in FIG. 2.

Figure 6:
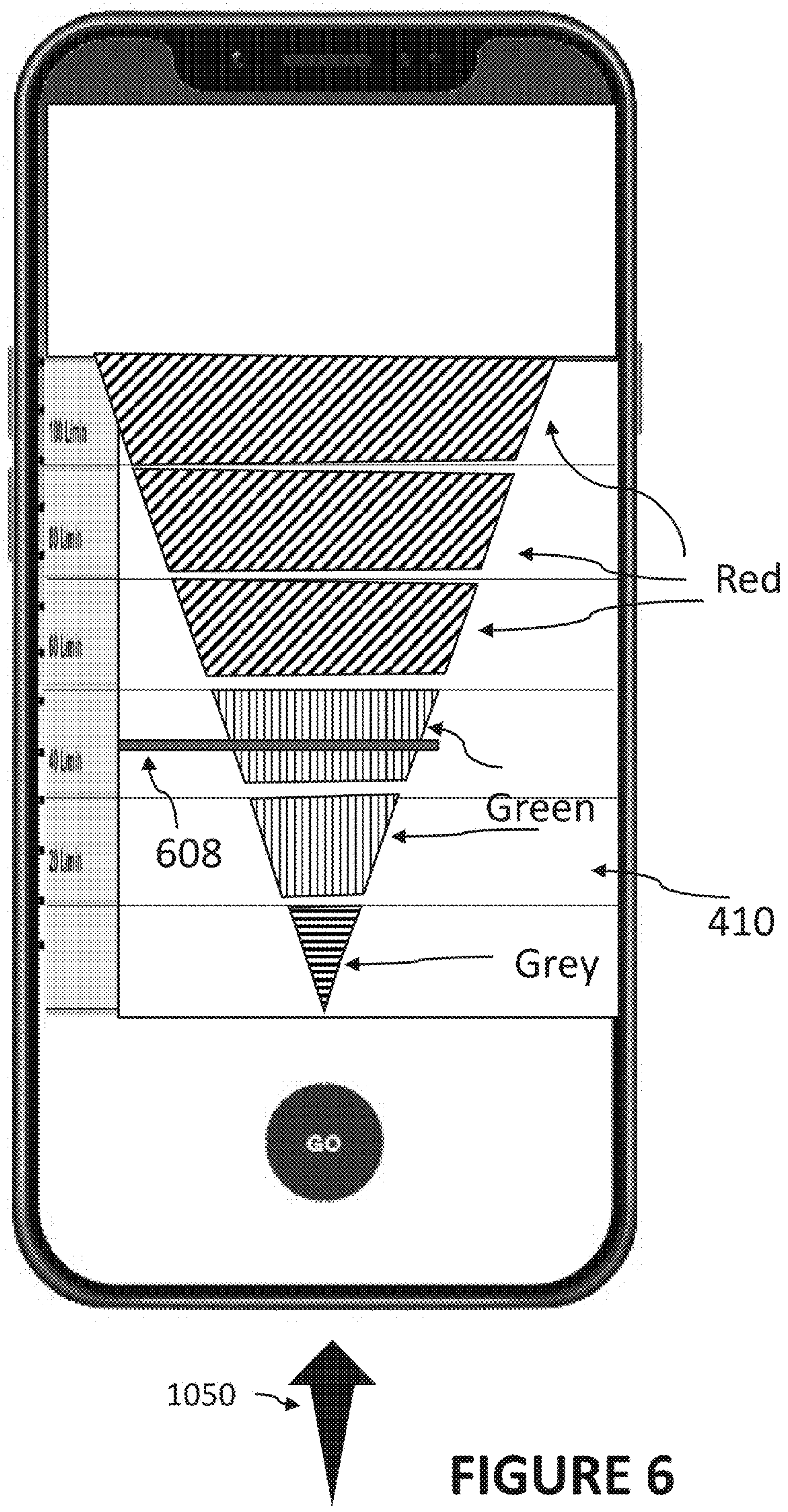
FIG. 6 is a front view illustrating a smartphone with a graphical user interface for showing a visual indicator (meter) which shows a visual indicator of the recorded sound intensity associated to an inhalation performed in close proximity to the smartphone integrated microphone, according to an embodiment of the invention.

FIG. 6 illustrates a front view of a smartphone with a graphical user interface for showing a visual indicator (meter) which shows a visual indicator of the recorded sound intensity associated to an inhalation performed in close proximity to the smartphone integrated microphone, according to an embodiment of the present technology. The touchscreen presents a scale corresponding to different values of the flow rate (which correspond to the recorded sound intensity). As such, green area located between 20 L/min and 60 L/min is presented with green color indicating to the user that, for the selected inhaler, the flow rate of between 20 L/min and 60 L/min is considered to be appropriate (optimal). Depending on the selected inhaler that was previously selected by the user 1012, the optimal range (green zone) for the inspiratory flow rate is rendered (displayed) in the display 1029. The optimal range may vary based on the type of the selected inhaler.

Figure 7:
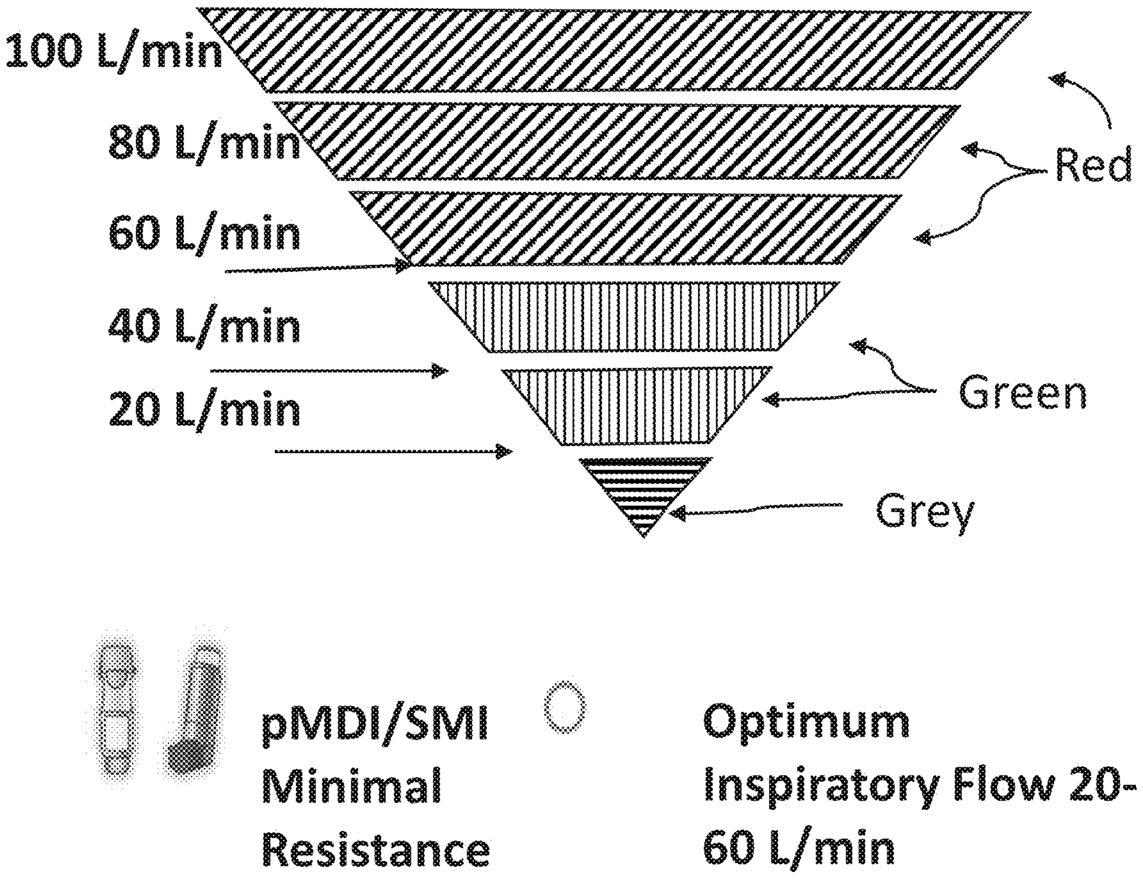
FIG. 7 is a range diagram illustrating an appropriate range of inhalation flow rate for using a pMDI or soft mist inhaler (SMI), according to an embodiment of the invention.
Figure 8:
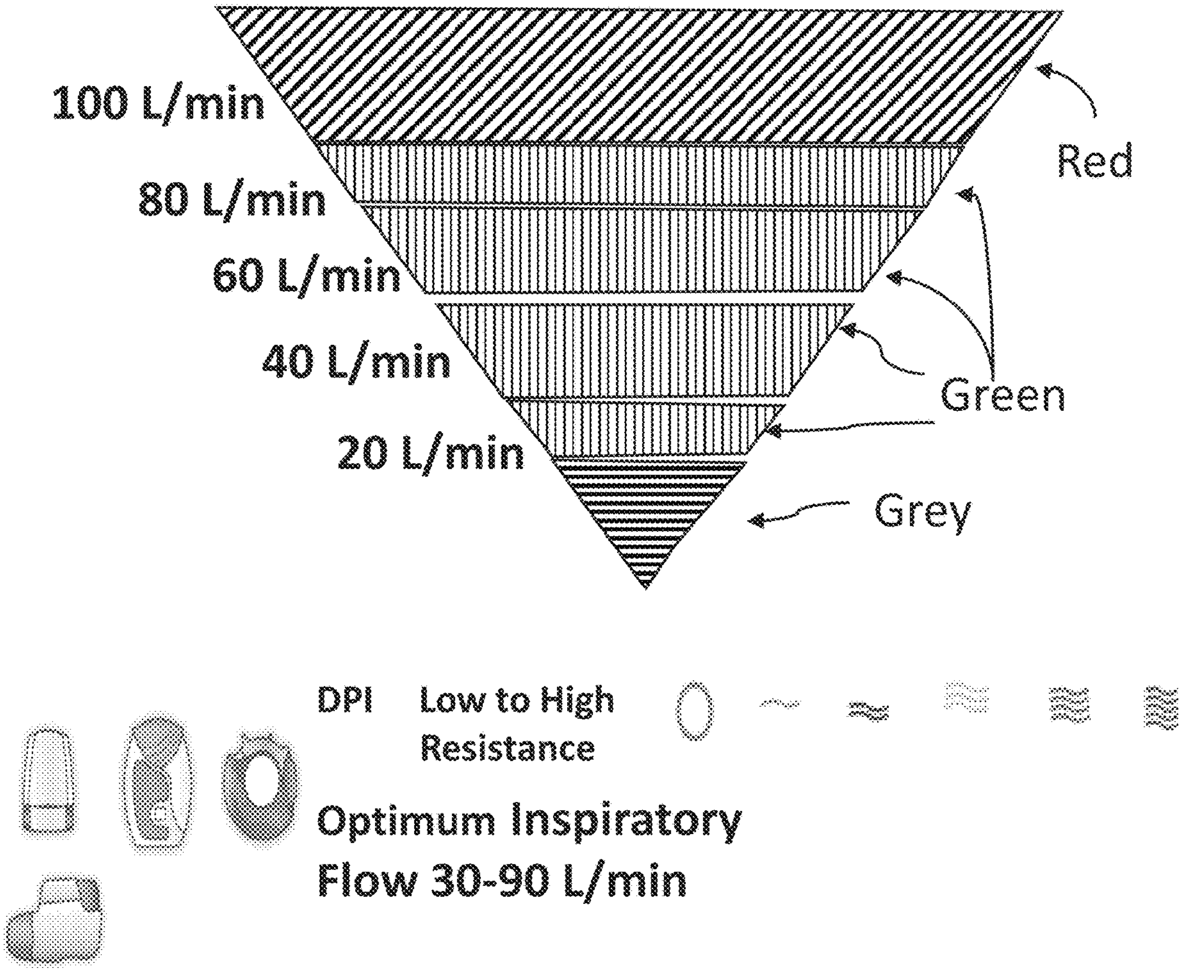
FIG. 8 is a range diagram illustrating an appropriate range of inhalation flow rate for using a DPI, according to an embodiment of the invention.

FIG. 7 illustrates a range diagram with an appropriate range of inhalation flow rate for using the selected inhaler when the selected inhaler is a pMDI or soft mist inhaler (SMI). The appropriate range is highlighted with green (and shown with vertical lines). FIG. 8 illustrates a range diagram with an appropriate range of inhalation flow rate for using the selected inhaler when the selected inhaler is of dry powder inhaler (DPI) type.

Referring again to FIG. 6, as the user inhales in close proximity to the microphone, measurements are recorded in the local database 1028 on the electronic device 1010. It is expected that the harder the user 1012 inhales, the higher the flow is (especially the peak flow rate) and the "reading" may be higher too.

The "reading" of the measurement may be provided, for example, by a "visual indicator" or a "visual meter 608". If the user has the sufficient inspiratory flow, a visual indicator 608 would land in the green zone for the particular selected inhaler. The visual indicator 608 may be of any form and is intended to indicate the value of the flow rate of the user 1012 achieved during the current measurement. The visual meter 608 is displayed in the display 1029 (touchscreen 410) to indicate that value of the user's inspiratory flow.

In other words, the local processor 1024 determines the value of the flow rate and displays the visual indicator 608 on the screen. The position of such visual meter 608 corresponds to the generated the value of the flow rate. If the position of the visual indicator 608 is located in the "green zone", that is, if the value of the flow rate is within the appropriate range of the flow rate for the selected inhaler, then the selected inhaler is considered to be one of appropriate inhalers for the user 1012.

Similar to the In-Check DIAL™, if the user 1012 has the sufficient inspiratory flow, the visual indicator 608 is displayed (lands) in the green zone for that particular selected inhaler.

The visual indicator 608 displayed on the display 1029 (touchscreen 410) corresponds to the value of the sound signal intensity of the sound of inhalation performed in close proximity to the microphone 1020. In addition to generating a visual picture of the correspondence of the user's flow rate to the appropriate flow rate, the processor determines if the inspiratory flow rate is within a predetermined range for the selected inhaler.

This is shown in FIG. 6, where the visual indicator 608 (also known as a meter) is shown, as well as the area on the actual device where the user is expected to perform inhalation mimicking the intensity of inhalation that he or she would have when using the inhaler.

The microphone in the electronic device 1010 then records the sound signal of the inhalation as described above and analyses the sound data to obtain the flow rate.

FIG. 7 shows an example where the pressurized meter dose inhaler (pMDI) type was previously selected by the user as the selected inhaler. For example, if the user receives a result in the range of 20-60 L/min (and thus the visual indicator 608 is in the green zone), then the local processor 1024 determines and confirms that the user is using the right (appropriate) inhaler (pMDI or SMI in this case).

It should be noted that the selected inhaler is considered "appropriate" for a specific user 1012 when the user 1012 is capable to achieve the flow rate that is within the predetermined range for that particular selected inhaler.

FIG. 8 shows an example if the dry powder inhaler (DPI) type was previously selected by the user 1012. If the user 1012 receives a result in the range of 30-90 L/min, then it would be a confirmation that the user is using the right device (DPI in this case).

Figure 9:
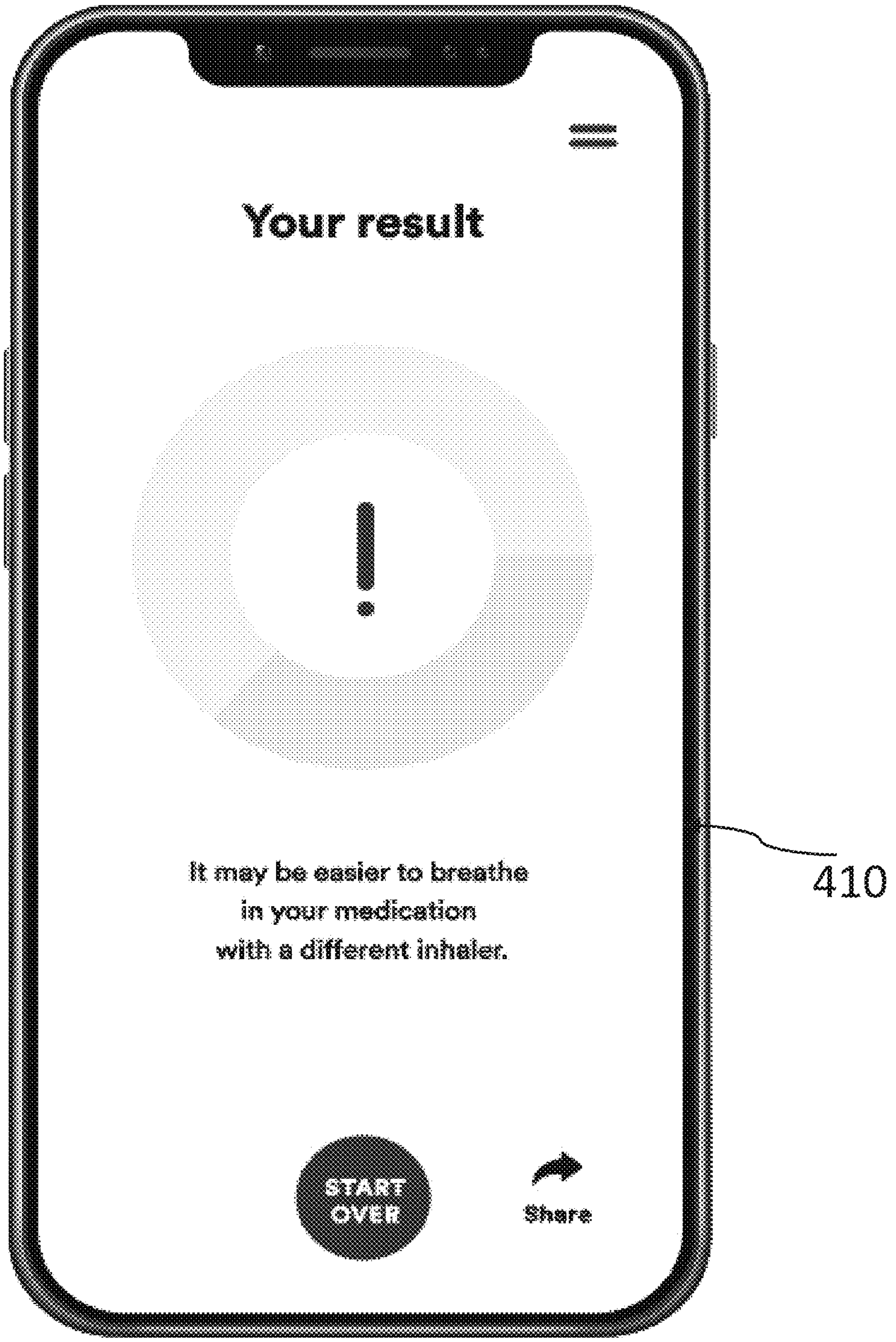
FIG. 9 is a front view illustrating a smartphone with a graphical user interface for showing a result of the suitability of the type of inhaler in view of the determination of the peak flow rate determined from the sound if inhalation, with a prompt to action when necessary, according to an embodiment of the invention.

As shown in FIG. 9, the conclusion message appears, with, for example, a call to action based on the result. For example, if the peak flow rate during inhalation is too weak, the conclusion message prompts (provides a call to action) to consider a different inhaler, as shown in FIG. 9. If the flow rate is determined to be appropriate for the selected inhaler, the conclusion message would indicate so instead to inform the user of the adequacy of the selected inhaler they are using or considering using.

At the end of the process, the application may suggest repeating the measurements (starting with selecting another inhaler, or repeating only the measurements) and re-direct to displaying one of the previous screens to redo inhalation measurements or to selected the inhaler. The application may also contain educational content on each type of inhaler or on each specific inhaler.

The system and method as described herein helps to simulate internal airflow resistance for all inhaler types, measure and predict an individual's peak inspiratory flow for specific inhalers, may help to render treatment inhaler decisions automatically and/or help support decisions of health care professionals (HCP). The system and method as described herein does not require face-to-face medical appointment, does not require additional equipment (only a smartphone), is sanitary (no mouthpiece required compared to medical devices available on the market), users can learn to inhale at the correct flow rate. The execution of the method is low-cost, simple and effective.

Figure 11:
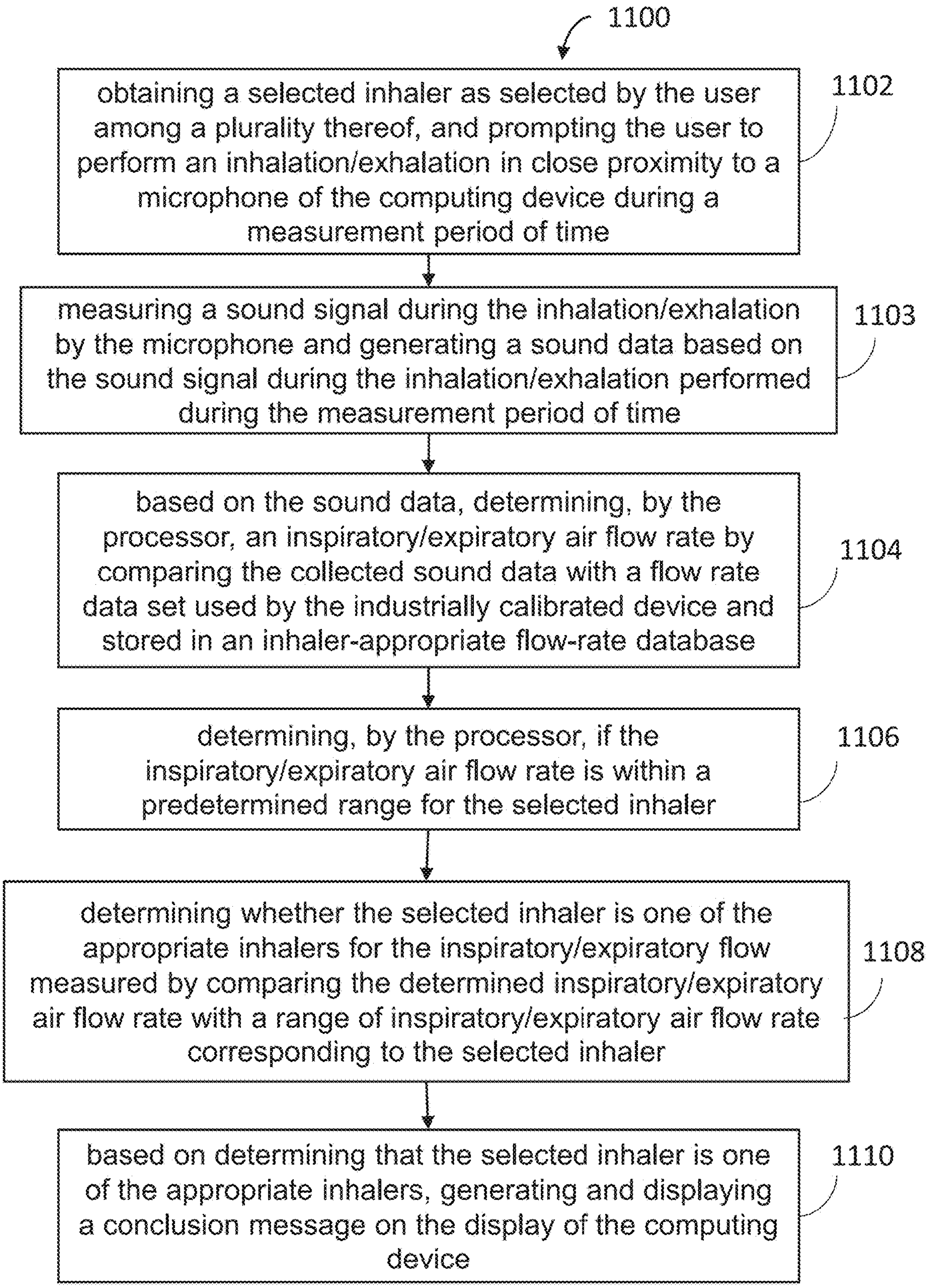
FIG. 11 illustrates a method for measuring an air flow rate from an inhalation to a microphone of an electronic device by a user is illustrated, in accordance with at least one embodiment of the present disclosure.

FIG. 11 illustrates a method 1100 for measuring an air flow rate from an inhalation to a microphone of an electronic device by a user, in accordance with at least one embodiment of the present disclosure. The steps of the method 1100 may be also performed to measure an expiratory air flow rate from an exhalation by prompting the user to exhale (instead of inhale) and by using the databases related to industrially calibrated devices adapted for measurement the expiratory air flow rate, as described above.

At step 1102, the user is prompted to select a type of an inhaler using the input device (such as, for example, the touchscreen) of the computing device. Through the input device 1034, the system 1000 receives the selected inhaler (in other terms, the inhaler selected by the user) among the plurality of the inhalers displayed on the display. The user is also prompted to perform an inhalation/exhalation in close proximity to the microphone of the computing device during a measurement period of time.

At step 1103, the system 1000, and in particular, the microphone, measures a sound signal and generates a sound data based on the sound signal during the inhalation/exhalation performed by the user during the measurement period of time.

At step 1104, based on the sound data, the local processor 1024 determines an inspiratory air flow rate/expiratory air flow rate by comparing the collected sound data with a flow rate data set used by the industrially calibrated device and stored in the calibration database 1055.

At step 1106, the local processor 1024 determines whether the inspiratory/expiratory flow rate is within a predetermined range for the type of inhaler selected by the user.

At step 1108, the local processor 1024 or the remote server 1040 determines whether the selected inhaler (or the selected type of the inhaler) is one of the appropriate inhalers (or appropriate types of the inhalers) for the inspiratory flow/expiratory flow measured.

At step 1110, based on determining that the selected inhaler (or the selected type of the inhaler) is one of the appropriate inhalers (appropriate types of the inhalers), the local processor 1024 or the remote server 1040 generates a conclusion message, which is then transmitted to and displayed on the display 1029 of the computing device 1010.

To determine the microphone sensitivity to be applied to the sound measured by the microphone 1020, to correspond to various resistances that are provided by the industrially-calibrated flow measurement devices, one may perform measurements with a group of subjects who asses their inspiratory efforts using the industrially-calibrated flow measurement devices and using the method and the software application as described herein. The microphone sensitivity database 1057 may be adjusted or corrected (or fine-tuned) by performing such measurements.

Measurements may be done in the same body position (e.g., sitting or standing), and resistance settings (which corresponds to a specific type of inhaler) in the industrially-calibrated flow measurement device are recorded when performing the measurement of the air flow with the industrially-calibrated flow measurement device. The measurements may be then performed for the same type of inhaler and by the same subject with the method and the software application on the electronic device 1010 as described above. The result of the measured flow rate may be also recorded and then compared to the results obtained with the industrially-calibrated flow measurement devices. For example, to determine the microphone sensitivity as provided in FIG. 3, a group of 7 subjects may be used to perform measurements, for example, 10 times, for each inhaler.

To obtain the microphone sensitivity, data was analyzed to determine if the microphone sensitivity and the industrially-calibrated flow measurement device both may have the same (or within a pre-determined deviation) flow rates expressed in L/min for each resistance setting.

For example, when the subject had the variation between 55 L/min and 65 L/min with Medium Low Resistance Setting in the In-Check Dial during 10 attempts, the average flow rate was determined to be 60.1 L/Min (and results variation being 10 for 10 attempts). This data was then compared with the same subject's flow rate measured with the system 1000 and the method 1100 as described herein and implemented using the software application, where the flow rate was measured at Medium Low Resistance Setting to be (using 10 attempts) between 53 L/min and 65 L/min, resulting in the average flow rate to be 60.6 L/Min (and results variation being 13 for 10 attempts).

Based on the analysis of such data for the In-Check Dial™ device, the microphone sensitivity database 1057 was adjusted by adjusting the microphone sensitivities to corresponding resistance settings, until the measurement results replicated each setting on the In-Check Dial™ device. Similarly, the microphone sensitivity database 1057 may be adjusted based on other industrially-calibrated flow measurement devices.

After each adjustment of the microphone sensitivity database 1057 as described, the parallel test measurements with the method 1100 and system 1000 and the industrially-calibrated flow measurement devices may be repeated to compare the flow rate (L/Min) measured with the application and with the industrially-calibrated flow measurement devices. The flow rate and the results variation may be thus compared for each inhaler or type of the inhaler.

Figure 12A:
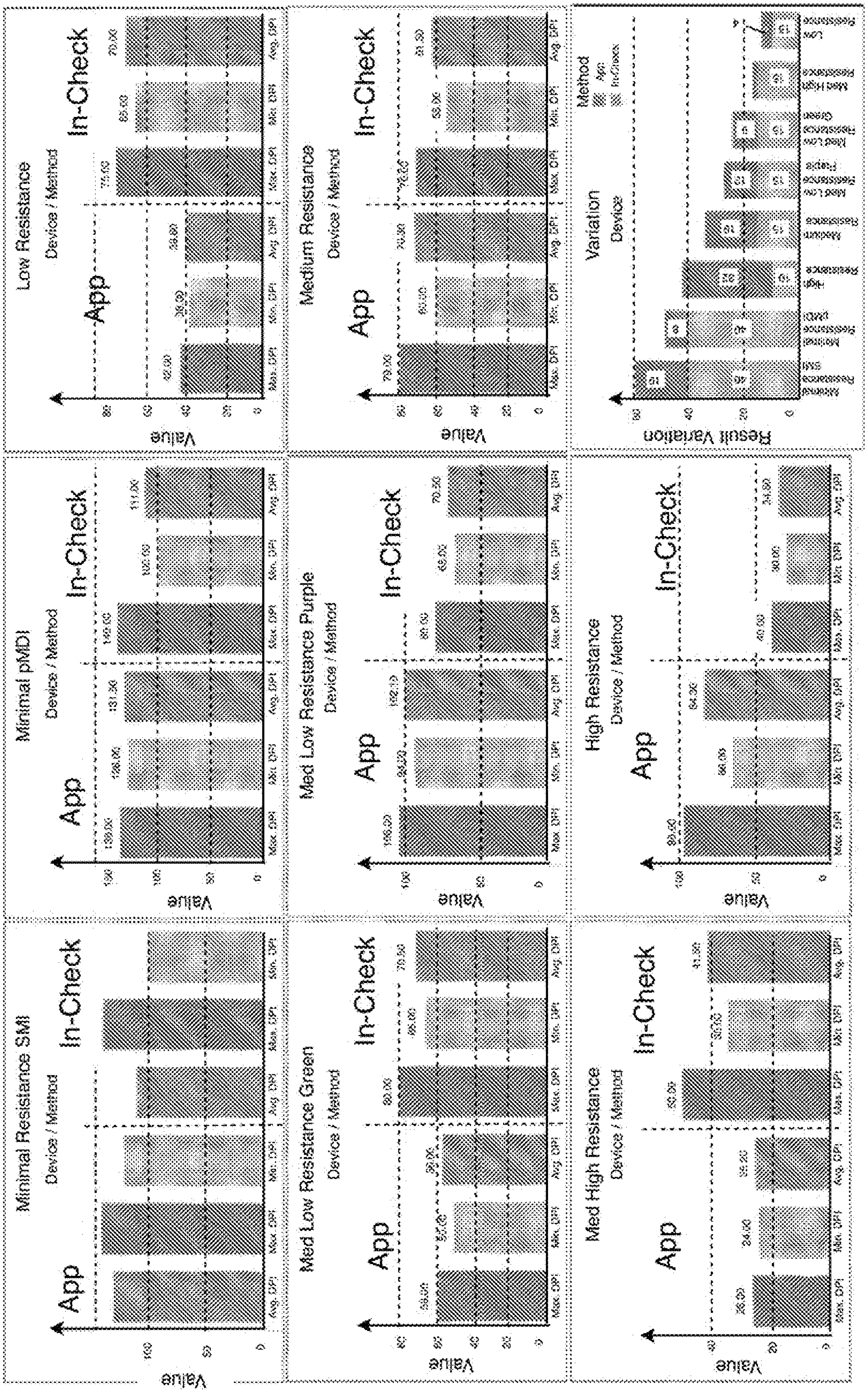
FIG. 12A depicts average, minimum and maximum values of flow rate measured for various DPI inhalers and various resistances when measured with the In-Check Dial™ device and the system and the method as described herein (implemented with a software application as described herein, referred to "App" in the drawings)
Figure 12B:
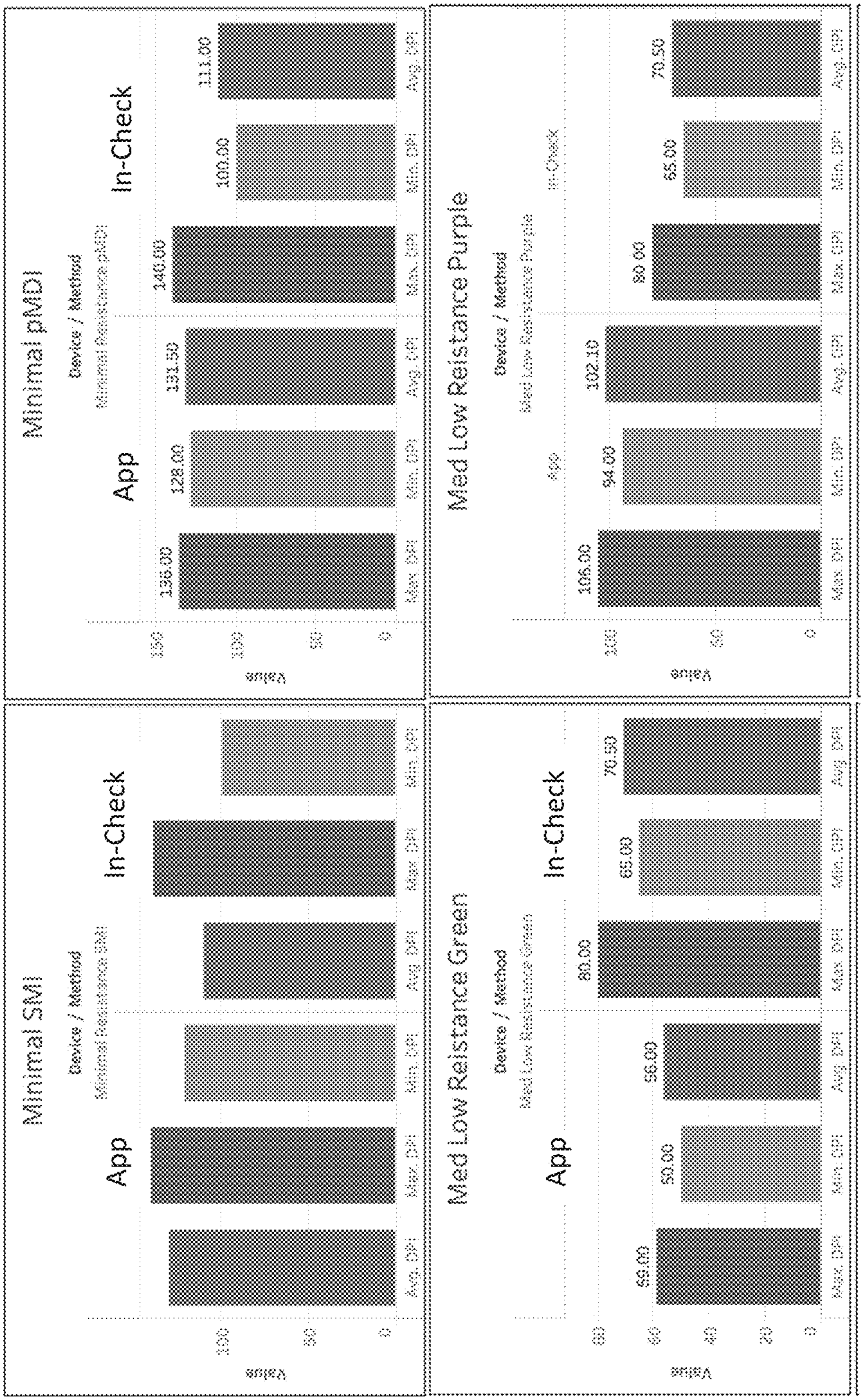
FIGS. 12B-12D depict various portions of FIG. 12A.
Figure 12C:
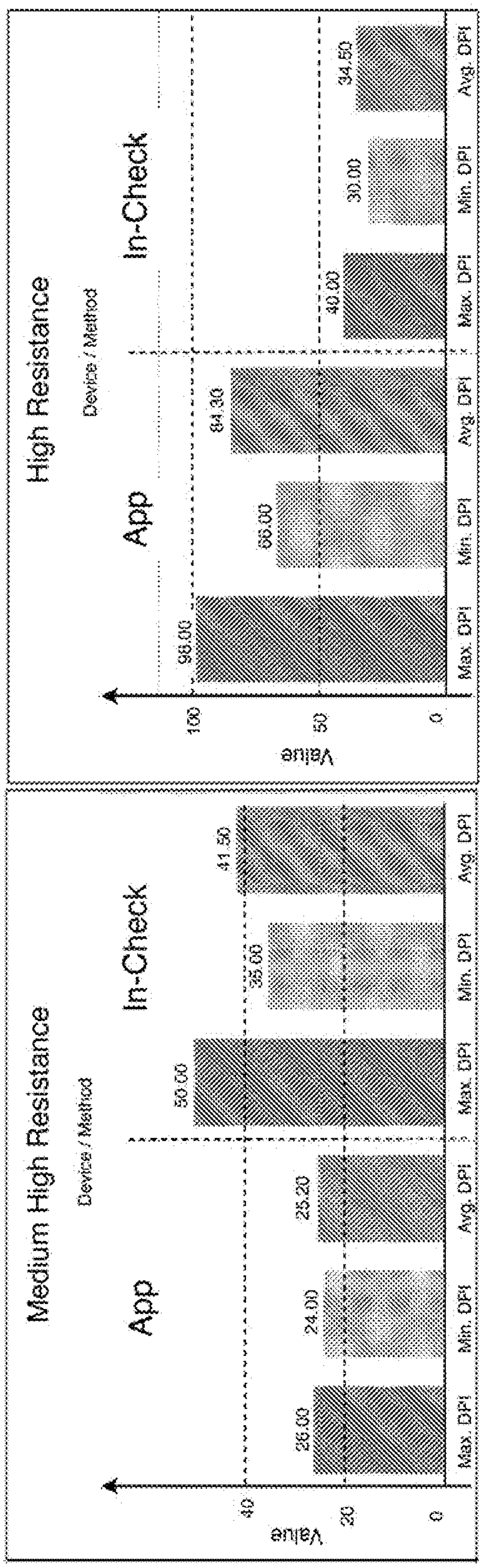
Figure 12D:
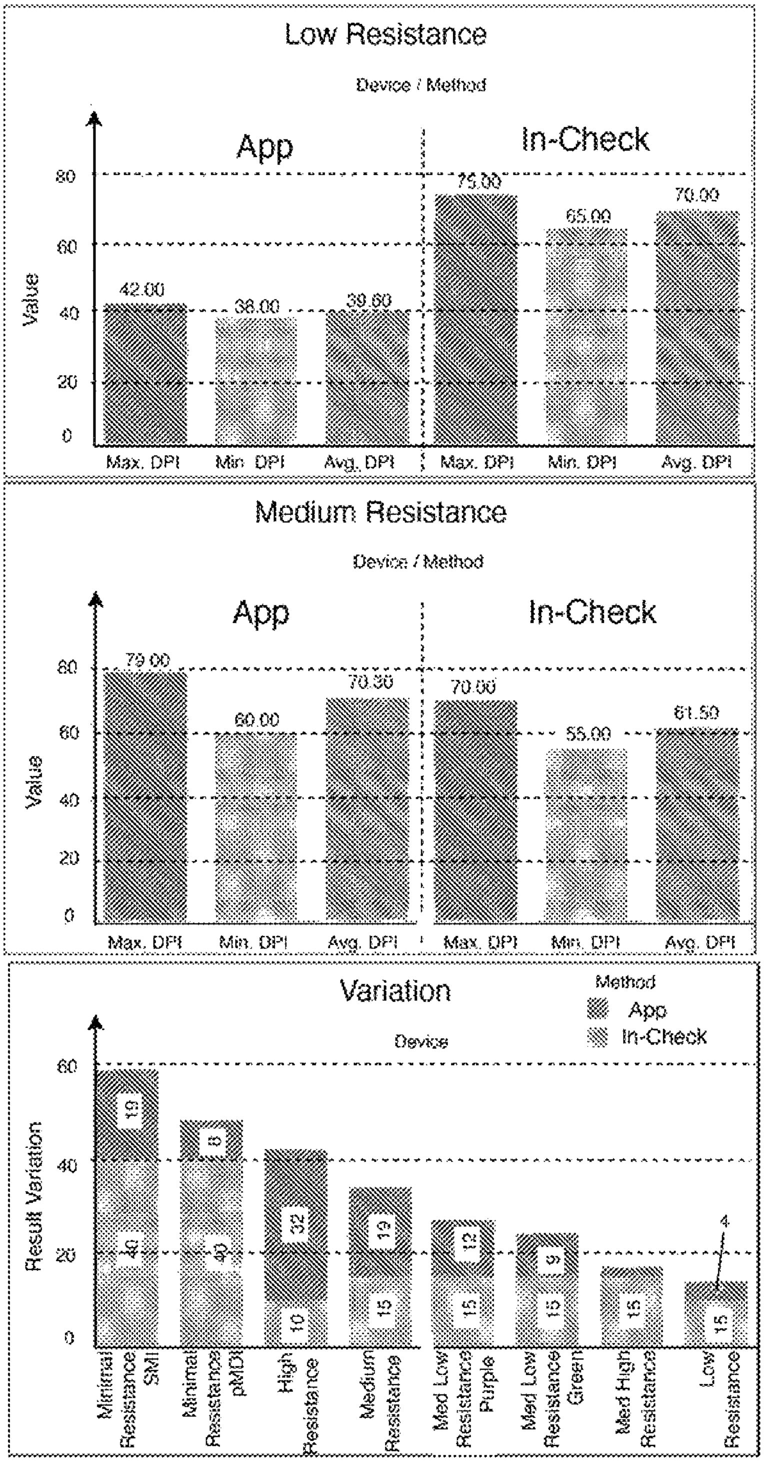

FIG. 12A depicts average, minimum and maximum values of flow rate measured for various DPI inhalers and various resistances when measured with the In-Check Dial™ device and the system 1000 and the method 1100 as described herein (implemented with a software application as described herein, referred to "App" in the drawings). FIGS. 12B-12D depict various portions of FIG. 12A.

Figure 13A:
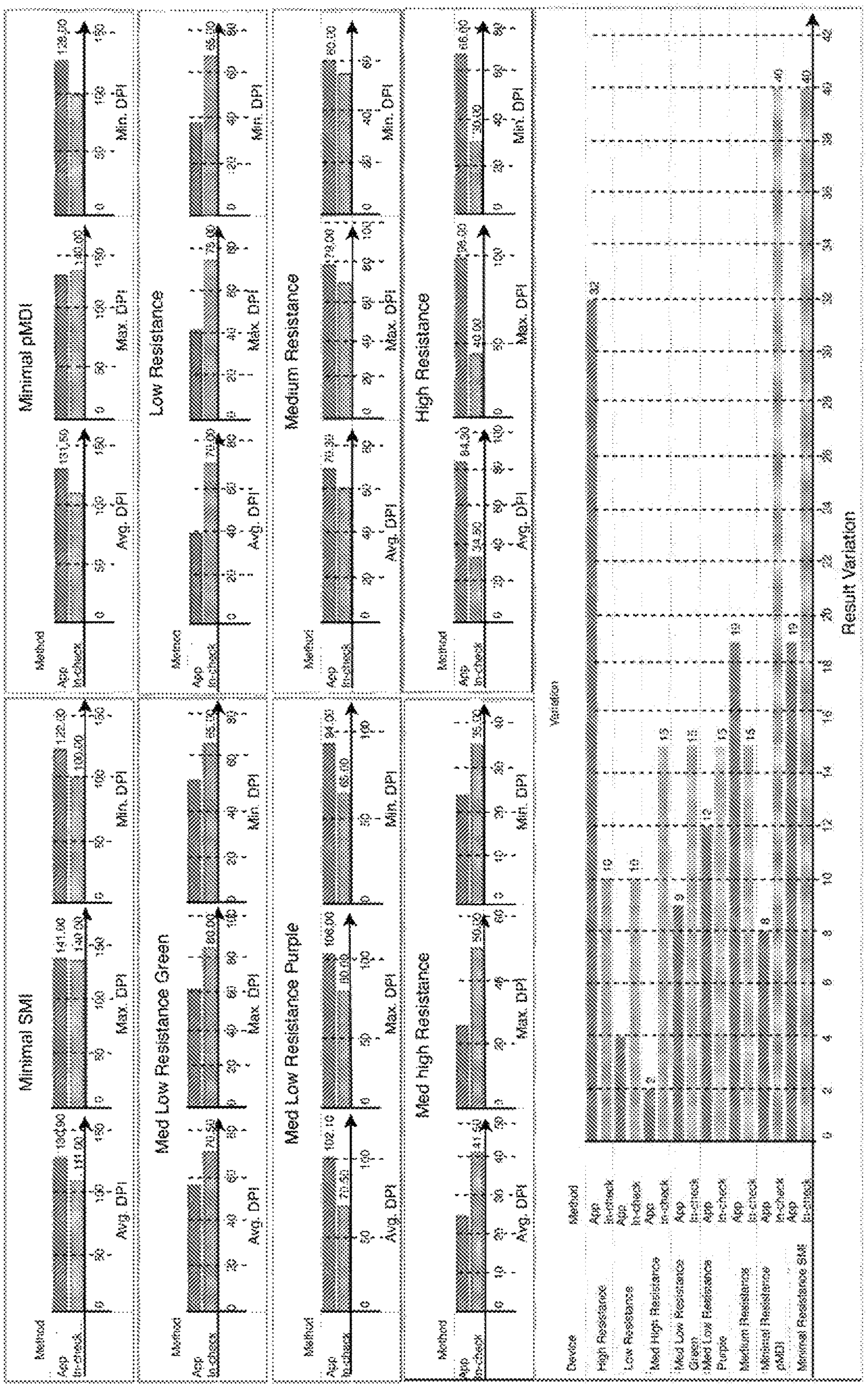
FIG. 13A compares results obtained with the In-Check Dial™ device and the system and the method as described herein (implemented with a software application as described herein, referred to "App" in the drawings)
Figure 13B:
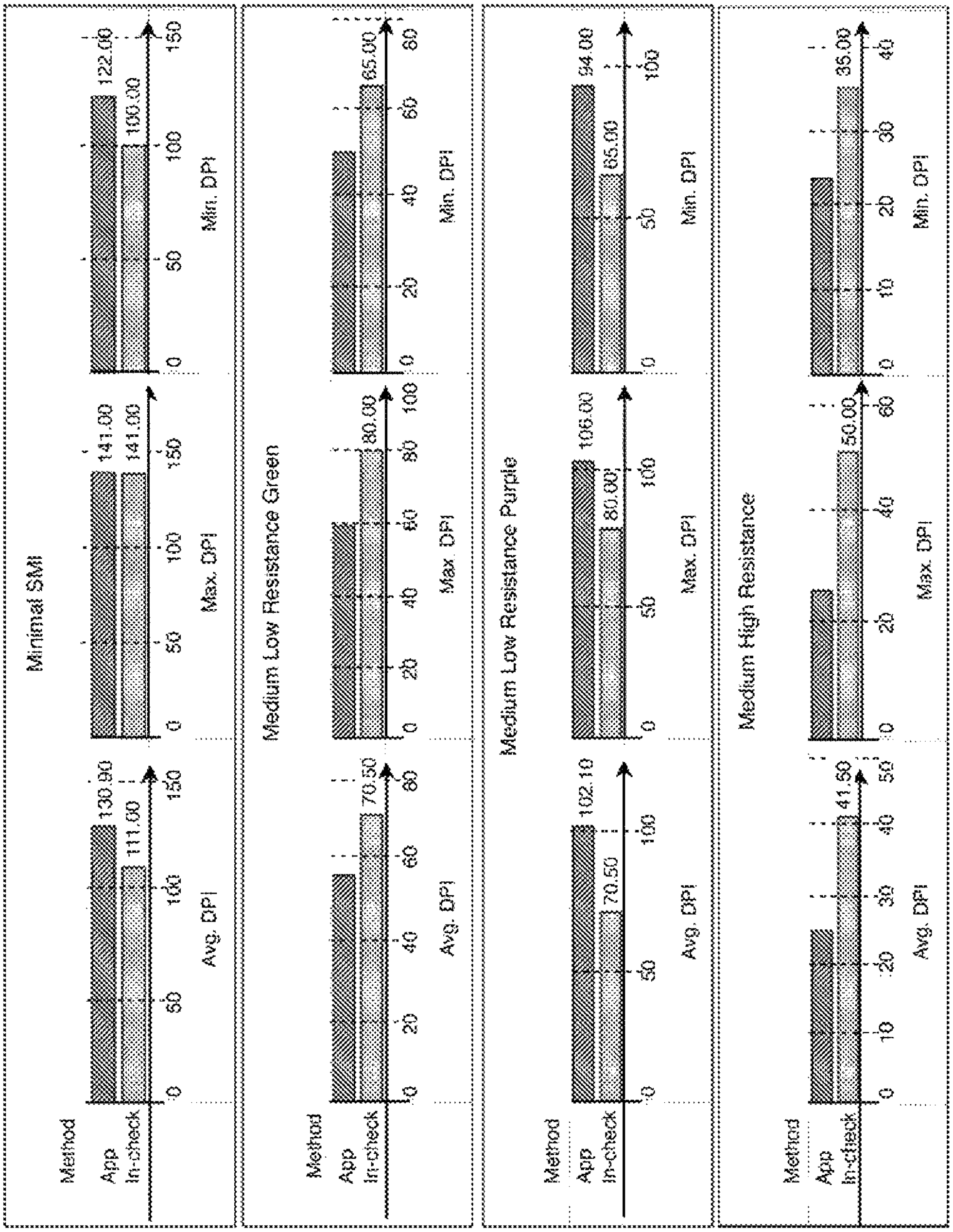
FIGS. 13B-13D depict various portions of FIG. 13A.
Figure 13C:
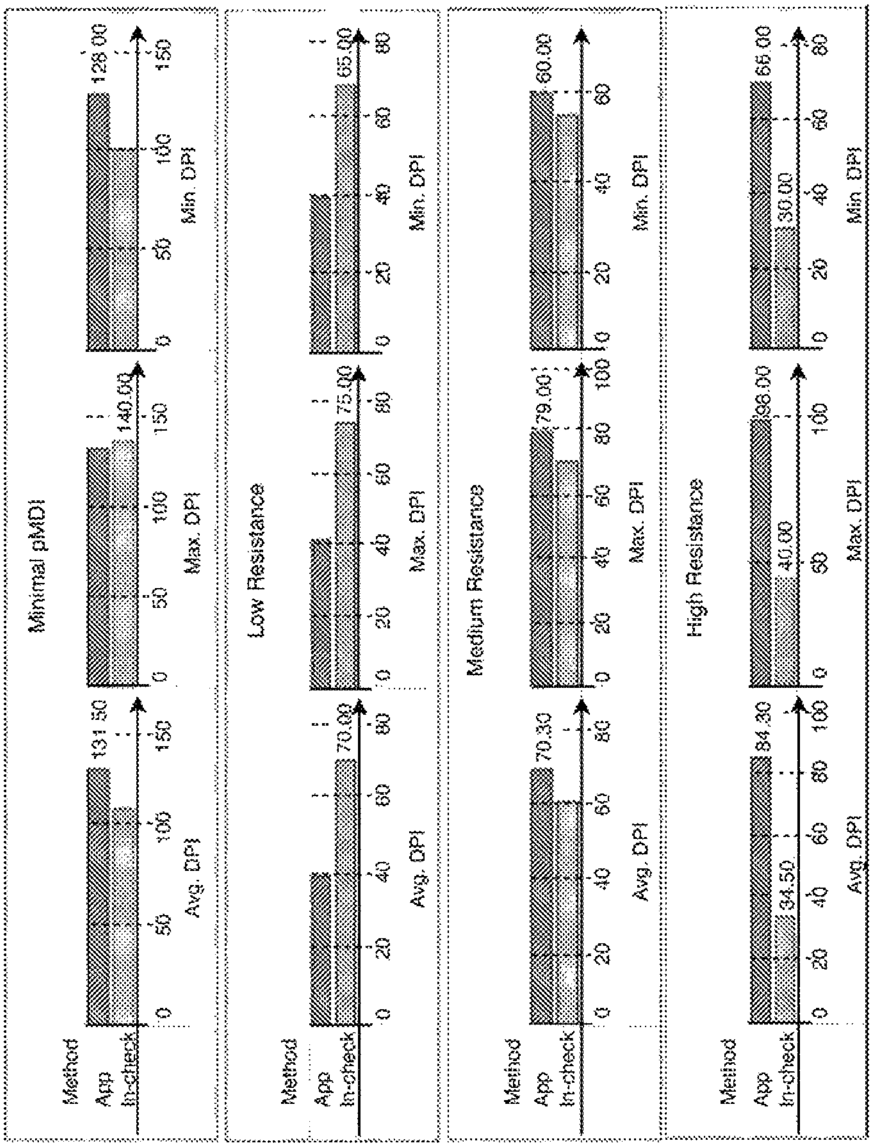
Figure 13D:
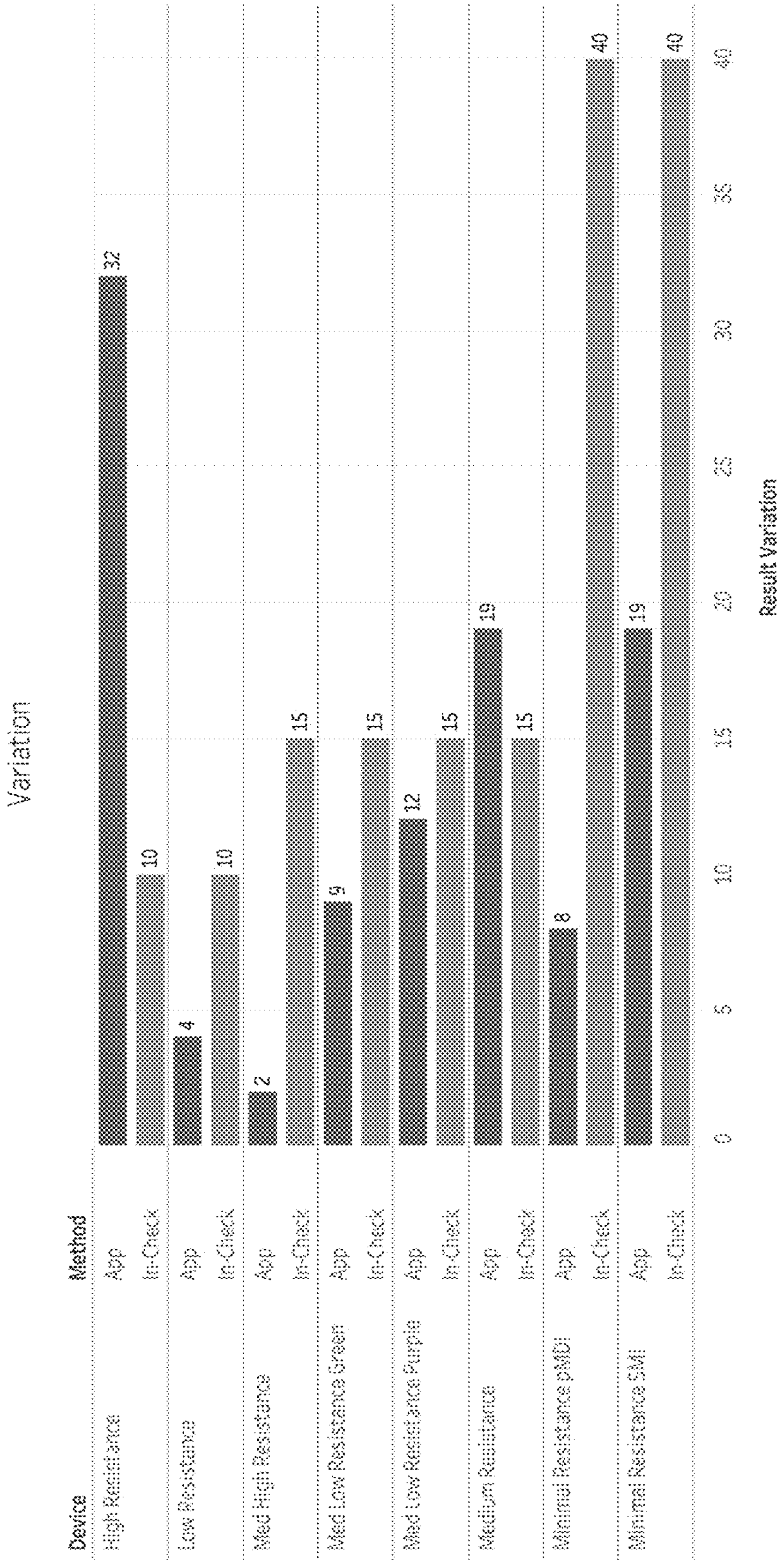

FIG. 13A compares results obtained with the In-Check Dial™ device and the system 1000 and the method 1100 as described herein (implemented with a software application as described herein, referred to "App" in the drawings). FIGS. 13B-13D depict various portions of FIG. 13A.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method for measuring an inspiratory/expiratory air flow rate from an inhalation/exhalation to a microphone of a personal computing device by a user, the personal computing device having a display and an input device, the method executable by a processor, the method comprising:

obtaining a selected inhaler as selected by the user among a plurality thereof, and prompting the user to perform an inhalation/exhalation in close proximity to the microphone of the personal computing device during a measurement period of time;

measuring by the microphone a sound signal during the inhalation/exhalation comprising a peak inspiratory flow rate, adjusting a microphone sensitivity to correlate with an inhaler resistance for the selected inhaler, and generating a sound data based on the sound signal measured during the inhalation/exhalation performed during the measurement period of time and further based on the microphone sensitivity adjusted to correlate with the inhaler resistance for the selected inhaler, the microphone sensitivity being a ratio, wherein one hundred percent of the microphone sensitivity corresponds to manufacturer's settings of the microphone;

based on the sound data, determining, by the processor, an inspiratory/expiratory air flow rate by comparing the collected sound data with a flow rate data set used by an industrially calibrated device and stored in an inhaler-appropriate flow-rate database;

determining, by the processor, if the inspiratory/expiratory air flow rate is within a predetermined range for the selected inhaler;

determining whether the selected inhaler is one of the appropriate inhalers for the inspiratory/expiratory flow measured by comparing the determined inspiratory/expiratory air flow rate with a range of inspiratory/expiratory air flow rate corresponding to the selected inhaler; and based on determining that the selected inhaler is one of the appropriate inhalers, generating and displaying a conclusion message on the display of the personal computing device wherein generating the sound data based on the sound signal comprises attenuating, by the processor, the sound signal measured by the microphone based on the microphone sensitivity determined for the selected inhaler, the microphone sensitivity being correlated to the inhaler resistance for the selected inhaler.

2. The method of claim 1, wherein the microphone sensitivity is determined by retrieving, from a microphone sensitivity database, a value of the microphone sensitivity associated with an inhaler identifier associated with the selected inhaler.

3. The method of claim 2, wherein the microphone sensitivity database is located locally on the personal computing device.

4. The method of claim 2, wherein the microphone sensitivity database is located remotely on a remote server.

5. The method of claim 1, further comprising adjusting the microphone sensitivity prior to measuring the sound data.

6. The method of claim 1, wherein generating and displaying the conclusion message on the display of the personal computing device that the selected type of the inhaler is one of the appropriate types of the inhaler in response to determining that the selected type of the inhaler is one of the appropriate types of the inhaler.

7. The method of claim 1, wherein the conclusion message is generated based on determining whether an inhaler identifier associated with the selected inhaler is within the range of inspiratory/expiratory air flow rate corresponding to the selected inhaler.

8. The method of claim 1, wherein the range of inspiratory/expiratory air flow rate corresponding to the selected inhaler is stored in a remote database located on a remote server.

9. The method of claim 1, wherein the selected inhaler comprises other inhalers being of the same type of the inhalers.

10. The method of claim 1, wherein the processor is the processor of the personal computing device.

11. The method of claim 1, wherein obtaining the selected inhaler comprises prompting the user to select, using the input device, an inhaler among inhalers rendered on the display to indicate the selected inhaler.

12. A system for measuring an air flow rate from an inhalation, the system comprising:

a display and an input device, a microphone sensitivity database comprising a plurality of pairs of microphone sensitivity values and inhaler identifiers;

an inhaler-appropriate flow-rate database comprising predetermined ranges for inhalers and inhaler identifiers; and a microphone of a personal computing device configured to measure a sound signal during inhalation/exhalation, a local processor coupled to a remote processor, both configured to:

receive a selection of an inhaler among inhalers rendered on the display to indicate a selected inhaler, and prompt a user to perform an inhalation/exhalation in close proximity to the microphone of the personal computing device during a measurement period of time, wherein the inhalation/exhalation comprises a peak inspiration flow rate;

adjust a microphone sensitivity to correlate with an inhaler resistance for the selected inhaler, the microphone sensitivity being a ratio, wherein one hundred percent of the microphone sensitivity corresponds to manufacturer's settings of the microphone;

generate, by the local processor, a sound data based on the sound signal measured during the inhalation/exhalation performed during the measurement period of time and further based on the microphone sensitivity adjusted to correlate with the inhaler resistance for the selected inhaler;

based on the sound data, determine an inspiratory/expiratory air flow rate by comparing the sound data with a flow rate data set used by an industrially calibrated device and stored in a calibration database;

determine whether the inspiratory/expiratory flow rate is within a predetermined range for the selected inhaler;

determine whether the selected inhaler is one of the appropriate inhalers for the inspiratory/expiratory flow measured by comparing the inspiratory/expiratory air flow rate with a range of inspiratory/expiratory air flow rate corresponding to the selected inhaler; and based on determining that the selected inhaler is one of the appropriate inhalers, generate a conclusion message on the display of the personal computing device, wherein the sound data being generated comprises the sound signal attenuated based on the microphone sensitivity determined for the selected inhaler, the microphone sensitivity being the ratio correlated to the inhaler resistance.

13. The system of claim 12, wherein the microphone sensitivity is determined by retrieving, from the microphone sensitivity database, a value of the microphone sensitivity associated with the inhaler identifier associated with the selected inhaler.

14. The system of claim 13, wherein the microphone sensitivity database is located locally on the personal computing device.

15. The system of claim 13, wherein the microphone sensitivity database is located remotely on a remote server.

16. The system of claim 12, wherein the microphone sensitivity is adjusted prior to measuring the sound data.

17. The system of claim 12, wherein the conclusion message is generated based on determining whether an inhaler identifier associated with the selected inhaler is within the range of inspiratory/expiratory air flow rate corresponding to the selected inhaler.

18. The system of claim 12, wherein the processor is the processor of the personal computing device.

19. A method for measuring an inspiratory/expiratory air flow rate from an inhalation/exhalation to a microphone of a personal computing device by a user, the personal computing device having a display and an input device, the method executable by a processor, the method comprising:

obtaining a selected inhaler as selected by the user among a plurality thereof, and prompting the user to perform an inhalation/exhalation comprising a peak inspiration flow rate in close proximity to the microphone of the personal computing device during a measurement period of time;

measuring a sound signal during the inhalation/exhalation by the microphone, adjusting a microphone sensitivity to correlate with an inhaler resistance for the selected inhaler as a ratio, and generating a sound data based on the sound signal measured during the inhalation/exhalation performed during the measurement period of time and based on the microphone sensitivity adjusted to correlate with the inhaler resistance for the selected inhaler, the microphone sensitivity being the ratio, wherein one hundred percent of the microphone sensitivity corresponds to manufacturer's settings of the microphone;

based on the sound data, determining, by the processor, an inspiratory/expiratory air flow rate by comparing the collected sound data with a flow rate data set used by an industrially calibrated device and stored in an inhaler-appropriate flow-rate database;

determining, by the processor, if the inspiratory/expiratory air flow rate is within a predetermined range for the selected inhaler;

determining whether the selected inhaler is one of the appropriate inhalers for the inspiratory/expiratory flow measured by comparing the determined inspiratory/expiratory air flow rate with a range of inspiratory/expiratory air flow rate corresponding to the selected inhaler, the range of inspiratory/expiratory air flow rate corresponding to the selected inhaler is stored in a remote database located on a remote server; and based on determining that the selected inhaler is one of the appropriate inhalers, generating and displaying a conclusion message on the display of the personal computing device.

* * * * *